(12) United States Patent
Mustakos et al.

(10) Patent No.: US 11,904,171 B2
(45) Date of Patent: Feb. 20, 2024

(54) TRANSLATION BETWEEN CATHODIC AND ANODIC NEUROMODULATION PARAMETER SETTINGS

(71) Applicant: Boston Scientific Neuromodulation Corporation, Valencia, CA (US)

(72) Inventors: Richard Mustakos, Simi Valley, CA (US); Stephen Carcieri, Los Angeles, CA (US); Chirag Shah, Valencia, CA (US); Peter J. Yoo, Burbank, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 68 days.

(21) Appl. No.: 17/460,532

(22) Filed: Aug. 30, 2021

(65) Prior Publication Data

US 2021/0387006 A1 Dec. 16, 2021

Related U.S. Application Data

(63) Continuation of application No. 16/396,256, filed on Apr. 26, 2019, now Pat. No. 11,123,563.
(Continued)

(51) Int. Cl.
- *A61N 1/36* (2006.01)
- *A61N 1/05* (2006.01)
- *G16H 20/30* (2018.01)

(52) U.S. Cl.
CPC ..... *A61N 1/36139* (2013.01); *A61N 1/36182* (2013.01); *A61N 1/36189* (2013.01);
(Continued)

(58) Field of Classification Search
CPC ............ A61N 1/36139; A61N 1/36182; A61N 1/36189; A61N 1/0534; A61N 1/0551;
(Continued)

(56) References Cited

U.S. PATENT DOCUMENTS

| 8,751,008 B2 | 6/2014 | Carlton et al. |
| 8,831,742 B2 | 9/2014 | Pianca et al. |

(Continued)

FOREIGN PATENT DOCUMENTS

| AU | 2016251663 B2 | 1/2019 |
| AU | 2019257732 B2 | 12/2021 |

(Continued)

OTHER PUBLICATIONS

"International Application Serial No. PCT/US2019/029260, International Preliminary Report on Patentability dated Nov. 5, 2020", 10 pgs.

(Continued)

*Primary Examiner* — Catherine M Voorhees
(74) *Attorney, Agent, or Firm* — Schwegman Lundberg & Woessner, P.A.

(57) ABSTRACT

A system for adjusting neuromodulation parameters used by a neuromodulator operably connected to a plurality of electrodes to modulate a neural target, may comprise a translation trigger detector configured to determine that a translation trigger has occurred, a first parameter setting storage configured to store first parameter settings for use by the neuromodulator to modulate the neural target, and a neuromodulation parameter translator. The neuromodulation parameter translator may be operably connected to the translation trigger detector to automatically translate the first parameter settings into a second parameter settings in response to determining the translation trigger has occurred, and replace the first parameter settings with the second parameter settings, or store the second parameter settings in a second parameter setting storage. Automatically translating may include either automatically translating from cathodic parameter settings to anodic parameter settings, or
(Continued)

automatically translating from anodic parameter settings to cathodic parameter settings.

20 Claims, 13 Drawing Sheets

Related U.S. Application Data

(60) Provisional application No. 62/663,541, filed on Apr. 27, 2018.

(52) U.S. Cl.
CPC .......... *A61N 1/0534* (2013.01); *A61N 1/0551* (2013.01); *A61N 1/36171* (2013.01); *G16H 20/30* (2018.01)

(58) Field of Classification Search
CPC ............ A61N 1/36171; A61N 1/36175; A61N 1/3615; G16H 20/30
See application file for complete search history.

(56) References Cited

U.S. PATENT DOCUMENTS

| | | | |
|---|---|---|---|
| 9,533,148 B2 | 1/2017 | Carcieri | |
| 9,561,380 B2 | 2/2017 | Carcieri et al. | |
| 9,855,432 B2 | 1/2018 | Yoo et al. | |
| 9,901,737 B2 | 2/2018 | Moffitt et al. | |
| 10,004,902 B2 | 6/2018 | Moffitt et al. | |
| 10,112,052 B2 | 10/2018 | Bokil et al. | |
| 10,173,055 B2 | 1/2019 | Howard et al. | |
| 10,195,446 B2 | 2/2019 | Howard et al. | |
| 11,123,563 B2 * | 9/2021 | Mustakos | A61N 1/36182 |
| 2011/0029040 A1 | 2/2011 | Walker et al. | |
| 2011/0160810 A1 | 6/2011 | Griffith | |
| 2011/0307032 A1 | 12/2011 | Goetz et al. | |
| 2013/0190838 A1 | 7/2013 | Caparso | |
| 2014/0277267 A1 * | 9/2014 | Vansickle | A61N 1/36071 607/46 |
| 2014/0364920 A1 | 12/2014 | Doan et al. | |
| 2015/0127062 A1 * | 5/2015 | Holley | A61N 1/37247 607/46 |
| 2015/0217116 A1 | 8/2015 | Parramon et al. | |
| 2015/0360038 A1 | 12/2015 | Zottola et al. | |
| 2016/0030749 A1 | 2/2016 | Carcieri et al. | |
| 2016/0030750 A1 | 2/2016 | Bokil et al. | |
| 2016/0082252 A1 * | 3/2016 | Hershey | A61N 1/36071 607/46 |
| 2016/0375248 A1 | 12/2016 | Carcieri et al. | |
| 2017/0056642 A1 | 3/2017 | Moffitt et al. | |
| 2017/0072207 A1 | 3/2017 | Howard et al. | |
| 2017/0087369 A1 | 3/2017 | Bokil et al. | |
| 2017/0157404 A1 | 6/2017 | Moffitt et al. | |
| 2017/0252570 A1 | 9/2017 | Serrano Carmona et al. | |
| 2017/0304636 A1 | 10/2017 | Steinke et al. | |
| 2017/0372039 A1 | 12/2017 | Mustakos et al. | |
| 2018/0028824 A1 | 2/2018 | Pivonka et al. | |
| 2018/0056068 A1 | 3/2018 | Zhang et al. | |
| 2018/0056073 A1 | 3/2018 | Torgerson | |
| 2018/0064930 A1 | 3/2018 | Zhang et al. | |
| 2018/0071516 A1 | 3/2018 | Weiss et al. | |
| 2018/0078776 A1 | 3/2018 | Mustakos et al. | |
| 2018/0085583 A1 | 3/2018 | Zhang et al. | |
| 2018/0104472 A1 | 4/2018 | Govea et al. | |
| 2018/0185650 A1 | 7/2018 | Shah | |
| 2018/0193655 A1 | 7/2018 | Zhang et al. | |
| 2018/0214687 A1 | 8/2018 | Nageri et al. | |
| 2018/0214699 A1 | 8/2018 | Kothandaraman et al. | |
| 2018/0214700 A1 | 8/2018 | Vansickle et al. | |
| 2018/0272142 A1 | 9/2018 | Zhang et al. | |
| 2018/0280698 A1 | 10/2018 | Steinke et al. | |
| 2019/0015039 A1 | 1/2019 | Blum et al. | |
| 2019/0054306 A1 | 2/2019 | Steinke et al. | |
| 2019/0099606 A1 | 4/2019 | Shah et al. | |
| 2019/0184171 A1 | 6/2019 | Mustakos et al. | |
| 2019/0329040 A1 | 10/2019 | Mustakos et al. | |

FOREIGN PATENT DOCUMENTS

| | | |
|---|---|---|
| EP | 2903687 B1 | 9/2016 |
| EP | 3197545 B1 | 1/2019 |
| WO | WO-2016019129 A1 | 2/2016 |
| WO | WO-2019210114 A1 | 10/2019 |
| WO | WO-2019210114 A2 | 10/2019 |
| WO | WO-2019210114 A3 | 12/2019 |

OTHER PUBLICATIONS

"International Application Serial No. PCT/US2019/029260, International Search Report dated Oct. 22, 2019", 6 pgs.
"International Application Serial No. PCT/US2019/029260, Invitation to Pay Additional Fees dated Aug. 19, 2019", 9 pgs.
"International Application Serial No. PCT/US2019/029260, Written Opinion dated Oct. 22, 2019", 8 pgs.
Mustakos, Richard, et al., "Systems and Methods for Clinical Effect-Based Neurostimulation,", U.S. Appl. No. 16/219,551, filed Dec. 13, 2018.
"Australian Application Serial No. 2019257732, First Examination Report dated May 14, 2021", 5 pgs.
"Australian Application Serial No. 2019257732, Response filed Nov. 29, 2021 to First Examination Report dated May 14, 2021", 23 pgs.
"European Application Serial No. 19730992.5, Invitation pursuant to Article 94(3) and Rule 71(1) EPC dated Feb. 2, 2023", 4 pgs.
"European Application Serial No. 19730992.5, Response filed Jun. 15, 2021 to Communication pursuant to Rules 161(1) and 162 EPC dated Dec. 15, 2021", 17 pgs.
U.S. Appl. No. 16/396,256, filed Apr. 26, 2019, Translation Between Cathodic and Anodic Neuromodulation Parameter Settings.
"U.S. Appl. No. 16/396,256, Examiner Interview Summary dated Feb. 22, 2021", 2 pgs.
"U.S. Appl. No. 16/396,256, Final Office Action dated Mar. 8, 2021", 18 pgs.
"U.S. Appl. No. 16/396,256, Non Final Office Action dated Nov. 20, 2020", 24 pgs.
"U.S. Appl. No. 16/396,256, Notice of Allowance dated May 26, 2021", 8 pgs.
"U.S. Appl. No. 16/396,256, Response filed Feb. 17, 2021 to Non Final Office Action dated Nov. 20, 2020", 19 pgs.
"U.S. Appl. No. 16/396,256, Response filed May 5, 2021 to Final Office Action dated Mar. 8, 2021", 12 pgs.

* cited by examiner

TRANSLATION BETWEEN CATHODIC AND ANODIC NEUROMODULATION PARAMETER SETTINGS

CLAIM OF PRIORITY

This application is a continuation of U.S. patent application Ser. No. 16/396,256, filed Apr. 26, 2019, which claims the benefit of priority under 35 U.S.C. § 119(e) of U.S. Provisional Patent Application Ser. No. 62/663,541, filed on Apr. 27, 2018, which are herein incorporated by reference in their entireties.

TECHNICAL FIELD

The present disclosure relates generally to medical devices, and more particularly, to neuromodulation systems, devices, and methods.

BACKGROUND

Neuromodulation, also referred to as neurostimulation, has been proposed as a therapy for a number of conditions. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neuromodulation, which may also be referred to as an implantable pulse generator (IPG), and one or more implantable leads each including one or more electrodes. The implantable neuromodulation delivers neuromodulation energy through one or more electrodes placed on or near a target site in the nervous system. An external programming device is used to program the implantable neuromodulation with parameters controlling the delivery of the neuromodulation energy. For example, the neuromodulation energy may be delivered in the form of electrical pulses using parameters that specify spatial (where to stimulate), temporal (when to stimulate), and informational (patterns of pulses directing the nervous system to respond as desired) aspects of a pattern of pulses.

The human nervous systems use neural signals having sophisticated patterns. Also, as the condition of the patient may change while receiving a neuromodulation therapy, the neuromodulation applied to the patient may need to be changed to maintain efficacy while minimizing the unintended and undesirable effects. Therefore, there is a need to provide neuromodulation systems capable of such complex neuromodulation and a need to provide efficient and accurate programming of such systems.

SUMMARY

This Summary includes examples that provide an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

An example (e.g. Example 1) of a system for adjusting neuromodulation parameters used by a neuromodulator operably connected to a plurality of electrodes to modulate a neural target, may comprise a translation trigger detector configured to determine that a translation trigger has occurred, a first parameter setting storage configured to store first parameter settings for use by the neuromodulator to modulate the neural target, and a neuromodulation parameter translator. The neuromodulation parameter translator may be operably connected to the translation trigger detector to automatically translate the first parameter settings into a second parameter settings in response to determining the translation trigger has occurred, and replace the first parameter settings with the second parameter settings, or store the second parameter settings in a second parameter setting storage. Automatically translating the first parameter settings into the second parameter settings may include either automatically translating from cathodic parameter settings to anodic parameter settings, or automatically translating from anodic parameter settings to cathodic parameter settings. The neuromodulator may be configured to use cathodic parameter settings for the neuromodulation parameters to deliver cathodic modulation to the neural target, and use anodic parameter settings for the neuromodulation parameters to deliver anodic modulation to the neural target. For example, the anodic parameter settings may include anodic monopolar, anodic pseudo-monopolar, and anodic major; and the cathodic parameter settings may include cathodic monopolar, cathodic pseudo-monopolar, and cathodic major.

In Example 2, the subject matter of Example 1 may optionally be configured such that the first parameter settings for the neuromodulation parameters include at least a polarity, an amplitude, and a fractionalization, and the neuromodulation parameter translator is configured to automatically translate the first parameter settings into the second parameter settings by changing the polarity for each active electrode in the plurality of electrodes.

In Example 3, the subject matter of Example 2 may optionally be configured such that the neuromodulation parameter translator is configured to automatically translate the first parameter settings into the second parameter settings by multiplying the amplitude by a scale factor. The scale factor may be determined based on whether the first parameter settings are characterized as cathodic, characterized as anodic, or characterized as balanced or relatively balanced between cathodic and anodic.

In Example 4, the subject matter of Example 2 may optionally be configured such that the neuromodulation parameter translator is configured to automatically translate the first parameter settings into the second parameter settings by multiplying the amplitude by a scale factor. An equation is used to determine the scale factor using one or more of: the polarity within the first parameter settings; the amplitude within the first parameter settings; a pulse width within the first parameter settings; a waveform within the first parameter settings; a frequency within the first parameter settings; at least one burst-related parameter within the first parameter settings; or one or more locations of modulation within the first parameter settings.

In Example 5, the subject matter of Example 2 may optionally be configured such that the neuromodulation parameter translator is configured to automatically translate the first parameter settings into the second parameter settings by multiplying the amplitude by a scale factor. The scale factor may be determined using a ratio between a first therapeutic range for the first parameter settings and a second therapeutic range for the second parameter settings, the first therapeutic range represents a range of amplitudes for the first parameter settings that extends from a therapeutic threshold to a side effect threshold. The second therapeutic range may represent a range of amplitudes for the second parameter settings that extends from a therapeutic threshold to a side effect threshold.

In Example 6, the subject matter of Example 2 may optionally be configured such that the neuromodulation parameter translator is configured to automatically translate the first parameter settings into the second parameter settings by multiplying the amplitude by a scale factor. A look-up table may be used to determine the scale factor, and at least one of the polarity, the pulse width, the amplitude, the waveform, the frequency, the at least one burst-related parameter, or the one or more locations of modulation may be used to index into the look-up table. The scale factor may be a nearest value or an interpolated value.

In Example 7, the subject matter of Example 2 may optionally be configured such that the neuromodulation parameter translator is configured to: construct a first table of Ith values for the fractionalization in the first parameter settings to characterize spatial points, wherein the first parameter settings provide a stimulation field model; determine a maximum radius of the stimulation field model at the amplitude for the first parameter settings; construct a second table of $I_{th}$ values for the second parameter settings to provide the stimulation field model with the maximum radius; determine, within the second table, a minimum value that provides the stimulation field model that equals or approximately equals the maximum radius; and use the determined minimum value, that provides the stimulation field model at the radius, as an amplitude for the second parameter settings.

In Example 8, the subject matter of Example 2 may optionally be configured such that the neuromodulation parameter translator is configured to: construct a first table characterizing spatial points for the fractionalization values in the first parameter settings, wherein the first parameter settings provide a first stimulation field model; determine a volume of a stimulation field model at the amplitude in the first parameter settings; construct a second table characterizing the spatial points for the second parameter settings to provide a second stimulation field model; determine an amplitude that provides the second stimulation field model with a volume that equals or approximately equals the first stimulation field model; and use the determined amplitude in the second parameter settings.

In Example 9, the subject matter of Example 1 may optionally be configured such that the system further comprises a user interface configured to receive at least one target region to be targeted using a neuromodulation field and zero or more avoidance regions to be avoided using the neuromodulation field. The controller may be configured to determine fractionalization values for the second parameter settings to modulate the at least one target region and avoid the zero or more avoidance regions. The user interface may be further configured to receive a polarity input indicating whether to provide anodic neuromodulation, cathodic neuromodulation or balanced or approximately balanced neuromodulation. The controller may be configured to control a polarity of neuromodulation provided by the neuromodulator according to the received polarity input.

In Example 10, the subject matter of Example 9 may optionally be configured such that the neuromodulation parameter translator may be configured to automatically translate the first parameter settings into the second parameter settings by changing the polarity of the neuromodulation, changing the fractionalization and changing the amplitude.

In Example 11, the subject matter of Example 10 may optionally be configured such that the neuromodulation parameter translator is configured to automatically translate the first parameter settings into the second parameter settings by optimizing the fractionalization and the amplitude for the second parameter settings to modulate a stimulation field model that corresponds to the first parameter settings.

In Example 12, the subject matter of Example 10 may optionally be configured such that the neuromodulation parameter translator is configured to automatically translate the first parameter settings into the second parameter settings by: constructing a first $I_{th}$ table for first fractionalization values in the first parameter settings to characterize spatial points, wherein the first parameter settings have an amplitude, a pulse width and a frequency; determining initial second fractionalization values for the second parameter settings based on the first fractionalization values, wherein elements of the initial second fractionalization values have an opposite polarity with respect to elements of the first fractionalization values, and constructing a second table using the initial second fractionalization values; determining a scaling factor for the initial fractionalization values in the second table to provide a scaled second table, wherein the scaling factor produces a minimum sum of the squares difference between the first table and the scaled second table; and optimizing the initial second fractionalization values into a second fractionalization values in the second table that has a least sum of the squared difference between the first table and the scaled second table.

In Example 13, the subject matter of any one or any combination of Examples 1-12 may optionally be configured such that the neuromodulation parameter translator is configured to use a fractionalization look-up table and use: a virtual electrode to index into the fractionalization look-up table to produce multipolar fractionalizations; or a virtual electrode to index into the fractionalization look-up table to produce monopolar fractionalizations.

In Example 14, the subject matter of any one or any combination of Examples 9-13 may optionally be configured such that the system includes a one-polarity major multipolar fractionalization look-up table for use in producing anodic major multipolar fractionalization or cathodic major multipolar fractionalization, a monopolar look-up table for use in producing anodic monopolar or cathodic monopolar fractionalizations, and a polarity-balanced look-up table.

In Example 15, the subject matter of any one or any combination of Examples 1-14 may optionally be configured such that the system further comprises a user interface configured to receive at least one of a polarity-specific region including a target region to be targeted using a neuromodulation field of a polarity type and zero or more avoidance regions to be avoided using the neuromodulation field of the polarity type. The polarity-specific region may be specific to one or more of cathodic major neuromodulation, anodic major neuromodulation, or balanced or relatively balanced neuromodulation. The controller may be configured to automatically translate the first parameter settings into the second parameter settings by determining fractionalization values for the second parameter settings based on the polarity-specific region.

An example (e.g. "Example 16") of a method for adjusting neuromodulation parameters used by a neuromodulator operably connected to a plurality of electrodes to modulate a neural target may include: determining that a translation trigger has occurred; and in response to determining that the translation trigger has occurred, automatically translating first parameter settings into second parameter settings. Automatically translating the first parameter settings into the second parameter settings may include either automatically translating from cathodic parameter settings to anodic parameter settings, or automatically translating from anodic parameter settings to cathodic parameter settings. The neuromodulator may be configured to use cathodic parameter settings for the neuromodulation parameters to deliver cathodic modulation to the neural target, and may be configured to use anodic parameter settings for the neuromodulation parameters to deliver anodic modulation to the neural target. For example, the anodic parameter settings may include anodic monopolar, anodic pseudo-monopolar, and anodic major; and the cathodic parameter settings may include cathodic monopolar, cathodic pseudo-monopolar, and cathodic major.

In Example 17, the subject matter of Example 16 may optionally be configured such that the first parameter settings for the neuromodulation parameters may include at least a polarity, an amplitude, and a fractionalization. Automatically translating the first parameter settings into the second parameter settings may include changing the polarity for each active electrode.

In Example 18, the subject matter of Example 17 may optionally be configured such that automatically translating the first parameter settings into the second parameter settings may include multiplying the amplitude by a scale factor. The scale factor may be determined based on whether the first parameter settings are characterized as cathodic, characterized as anodic, or characterized as balanced or relatively balanced between cathodic and anodic.

In Example 19, the subject matter of Example 17 may optionally be configured such that automatically translating the first parameter settings into the second parameter settings may include multiplying the amplitude by a scale factor. An equation may be used to determine the scale factor using one or more of: the polarity within the first parameter settings; the amplitude within the first parameter settings; a pulse width within the first parameter settings; a waveform within the first parameter settings; a frequency within the first parameter settings; at least one burst-related parameter within the first parameter settings; or one or more locations of modulation within the first parameter settings.

In Example 20, the subject matter of Example 17 may optionally be configured such that automatically translating the first parameter settings into the second parameter settings may include multiplying the amplitude by a scale factor. The scale factor may be determined using a ratio between a first therapeutic range for the first parameter settings and a second therapeutic range for the second parameter settings. The first therapeutic range may represent a range of amplitudes for the first parameter settings that extends from a therapeutic threshold to a side effect threshold, and the second therapeutic range may represent a range of amplitudes for the second parameter settings that extends from a therapeutic threshold to a side effect threshold.

In Example 21, the subject matter of Example 17 may optionally be configured such that automatically translating the first parameter settings into the second parameter settings may include multiplying the amplitude by a scale factor. A look-up table may be used to determine the scale factor, and at least one of the polarity, the pulse width, the amplitude, the waveform, the frequency, the at least one burst-related parameter, or the one or more locations of modulation may be used to index into the look-up table. The scale factor may be a nearest value or an interpolated value.

In Example 22, the subject matter of Example 17 may optionally be configured such that the method further comprises: constructing a first table of $I_{th}$ values for the fractionalization in the first parameter settings to characterize spatial points, wherein the first parameter settings provide a stimulation field model; determining a maximum radius of the stimulation field model at the amplitude for the first parameter settings; constructing a second table of $I_{th}$ values to characterize the spatial points for the second parameter settings to provide the stimulation field model with the maximum radius; determining, within the second table, a minimum value that provides the stimulation field model that equals or approximately equals the maximum radius, and using the determined minimum value, that provides the stimulation field model at the radius, as an amplitude for the second parameter settings.

In Example 23, the subject matter of Example 17 may optionally be configured such that the method further comprises: constructing a first table characterizing spatial points for the fractionalization values in the first parameter settings, wherein the first parameter settings provide a first stimulation field model; determining a volume of a stimulation field model at the amplitude in the first parameter settings; constructing a second table characterizing the spatial points for the second parameter settings to provide a second stimulation field model; determining an amplitude that provides the second stimulation field model with a volume that equals or approximately equals the first stimulation field model; and using the determined amplitude in the second parameter settings.

In Example 24, the subject matter of Example 16 may optionally be configured such that the method further comprises: receiving at least one target region to be targeted using a neuromodulation field and zero or more avoidance regions to be avoided using the neuromodulation field, and determining fractionalization values for the second parameter settings to modulate the at least one target region and avoid the zero or more avoidance regions; and receiving a polarity input indicating whether to provide anodic neuromodulation, cathodic neuromodulation or balanced or approximately balanced neuromodulation, and controlling a polarity of neuromodulation provided by the neuromodulator according to the received polarity input.

In Example 25, the subject matter of Example 24 may optionally be configured such that automatically translating the first parameter settings into the second parameter settings may include changing the polarity of the neuromodulation, changing the fractionalization and changing the amplitude.

In Example 26, the subject matter of Example 25 may optionally be configured such that automatically translating the first parameter settings into the second parameter settings may include optimizing the fractionalization and the amplitude for the second parameter settings to modulate a stimulation field model that corresponds to the first parameter settings.

In Example 27, the subject matter of Example 25 may optionally be configured such that automatically translating the first parameter settings into the second parameter settings may include: constructing a first $I_{th}$ table for first fractionalization values in the first parameter settings to characterize spatial points, wherein the first parameter settings have an amplitude, a pulse width and a frequency; determining initial second fractionalization values for the second parameter settings based on the first fractionalization values, wherein elements of the initial second fractionalization values have an opposite polarity with respect to elements of the first fractionalization values, and constructing a second table using the initial second fractionalization values; determining a scaling factor for the initial fractionalization values in the second table to provide a scaled second table, wherein the scaling factor produces a minimum sum of the squares difference between the first table and the scaled second table; and optimizing the initial second fractionalization values into a second fractionalization values in the second table that has a least sum of the squared difference between the first table and the scaled second table.

In Example 28, the subject matter of Example 16 may optionally be configured such that the method further comprises using a virtual electrode to index into the fractionalization look-up table to produce multipolar fractionalizations.

In Example 29, the subject matter of Example 16 may optionally be configured such that the method further comprises using steering coordinates, including z axis, rotation, and spread coordinates, to index into the fractionalization look-up table to produce monopolar fractionalizations.

In Example 30, the subject matter of Example 16 may optionally be configured such that the method further comprises using a one-polarity major multipolar fractionalization look-up table to produce anodic major multipolar fractionalization or cathodic major multipolar fractionalization.

In Example 31, the subject matter of Example 16 may optionally be configured such that the method further comprises using a monopolar look-up table to produce anodic monopolar or cathodic monopolar fractionalizations.

In Example 32, the subject matter of Example 16 may optionally be configured such that the method further comprises using a monopolar look-up table to produce polarity-balanced fractionalizations.

In Example 33, the subject matter of Example 16 may optionally be configured such that the method further comprises receiving at least one of a polarity-specific region including a target region to be targeted using a neuromodulation field of a polarity type and zero or more avoidance regions to be avoided using the neuromodulation field of the polarity type. The polarity-specific region may be specific to one or more of cathodic major neuromodulation, anodic major neuromodulation, or balanced or relatively balanced neuromodulation. Automatically translating the first parameter settings into the second parameter settings may include determining fractionalization values for the second parameter settings based on the polarity-specific region.

An example (e.g. "Example 34") includes a non-transitory computer-readable medium having computer executable instructions stored thereon that, when executed by at least one processor, cause the at least one processor to perform the instructions to adjust neuromodulation parameters for use by a neuromodulator operably connected to a plurality of electrodes to modulate a neural target, The instructions may be capable of performing the methods recited above. For example, the instructions may comprise cause the machine to: determine that a translation trigger has occurred, and in response to determining that the translation trigger has occurred, automatically translate first parameter settings into second parameter settings. Automatically translating the first parameter settings into the second parameter settings may include either automatically translating from cathodic parameter settings to anodic parameter settings, or automatically translating from anodic parameter settings to cathodic parameter settings. The neuromodulator may be configured to use cathodic parameter settings for the neuromodulation parameters to deliver cathodic modulation to the neural target, and may be configured to use anodic parameter settings for the neuromodulation parameters to deliver anodic modulation to the neural target.

In Example 35, the subject matter of Example 14 may optionally be configured such that the first parameter settings for the neuromodulation parameters include at least a polarity, an amplitude, and a fractionalization. Automatically translating the first parameter settings into the second parameter settings may include changing the polarity for each active electrode.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
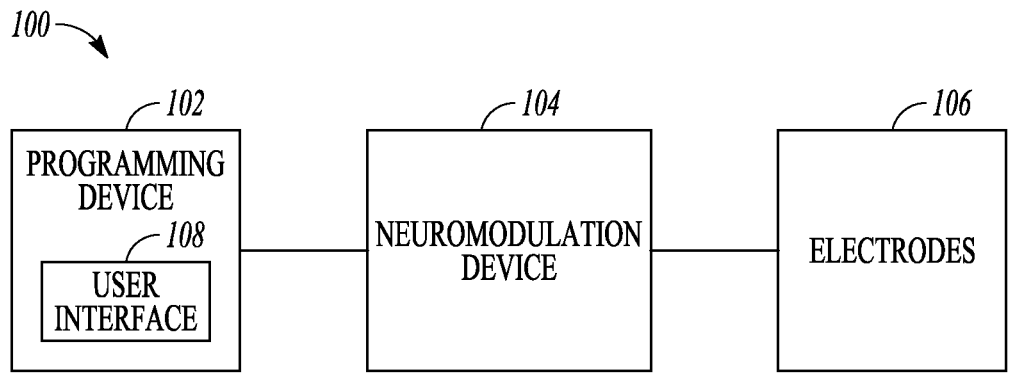
FIG. 1 illustrates, by way of example and not limitation, an embodiment of a neuromodulation system.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Different types of neural structures have different reactions to different neuromodulation polarities. For example, cathodic neuromodulation may have a tendency to preferentially modulate neuron fibers, and anodic neuromodulation may have a tendency to preferentially modulate tissue inclusive of cell bodies. Although conventional DBS has used cathodic neuromodulation, it is believed that anodic neuromodulation for DBS may benefit some patients more than cathodic stimulation. Thus, it is believed that a particular disease may response better to anodic stimulation, and another disease may respond better to cathodic stimulation, and yet another disease may response better to a mixed or balanced or nearly balanced neuromodulation (at least some percentage of anodic neuromodulation and at least some percentage of cathodic neuromodulation). Further, cathodic neuromodulation of one region may improve one or more symptoms of a disease and anodic neuromodulation of the same or different region may improve one or more other symptoms of the disease. Additional properties of the neuromodulation therapy may also contribute to the preferential modulation of some tissue over other tissue. Examples of such properties may include proximity of the tissue to an electrode, the size of the neural element, the trajectory/geometry of the neural element, the proximity of the cell body (or dendrites, or axon), the biophysical properties such as ion channels and distribution in the neural element, the synaptic machinery of the neural element, and the like.

Since different neural tissue have different responses to different neuromodulation polarities, the process for programming modulation parameters to target some region(s) while avoiding other region(s) can be complex. However, clinicians currently do not have any direction on how to convert from cathodic settings to anodic settings.

Various embodiments provided herein automatically translate between cathodic and anodic neuromodulation parameter settings. For example, various embodiments automatically translate cathodic settings, which may have been previously programmed into the neuromodulation system, into anodic settings. Similarly, various embodiments may automatically convert anodic settings into cathodic settings. For example, various embodiments may be used to invert the polarity of the original settings, with or without changing the fractionalization of the current among the electrodes. Various embodiments may automatically convert the cathodic settings to anodic settings using known target and avoidance regions. Each region may have an associated weight, which may be shared between regions, a background weight, possibly voxelization settings, and possibly a stimulation type. As will be discussed further below, stimulation type examples may include anodic monopolar, cathodic monopolar, anodic major, cathodic major, and balanced. Some system embodiments allow the user to set the neuromodulation polarity to any of these types.

In various examples, the neuromodulation system may include an implantable device configured to deliver neuromodulation therapies, such as DBS, SCS and PNS including vagus nerve stimulation (VNS), and one or more external devices configured to program the implantable device for its operations and monitor the performance of the implantable device. While DBS is discussed as a specific example, the present subject matter may also be applied to program stimulation devices for delivering various types of neuromodulation therapies.

The neuromodulation system may determine one or more stimulation parameters to modulate a target, such as a stimulation current and an electrical current fractionalization across a plurality of electrodes. The current fractionalization refers to current distribution among electrodes, and may be represented by percentage cathodic current, percentage anodic current, or off (no current allocation). Although current fractionalization is discussed in this document, it is to be understood that voltage or electrical energy may similarly be fractionalized among the electrodes, which may result in a particular spatial distribution of the stimulation field.

FIG. 1 illustrates, by way of example and not limitation, an embodiment of a neuromodulation system 100. The system 100 may, for example, be configured for DBS applications. Such DBS configuration includes various features that may simplify the task of the user in programming the stimulation device 104 for delivering DBS to the patient, such as the features discussed in this document. The illustrated system 100 includes a programming device 102, a neuromodulation device 104, and electrodes 106. The electrodes 106 may be configured for placement on or near one or more neural targets in a patient. The stimulation device 104 may be configured to be electrically connected to the electrodes 106 and deliver neuromodulation energy, such as in the form of electrical pulses, to the one or more neural targets though the electrodes 106. In an example, the neuromodulation device 104 controls the delivery of neuromodulation energy according to a plurality of neuromodulation parameters, such as a selection of active electrodes for passing neuromodulation energy to the tissue, or stimulation pattern of the electrical pulses, among others. In various examples, at least some of the neuromodulation parameters are programmable by a user, such as a clinician.

The programming device 102 may be configured to be in communication with the neuromodulation device 104 via a wired or wireless link. The programming device 102 may provide the user with accessibility to user-programmable parameters. In the illustrated example, the programming device 102 may include a user interface 108 that allows a user to control the operation of the system 100 and monitor the performance of the system 100 as well as conditions of the patient including responses to the delivery of the neuromodulation. The user may control the operation of the system 100 by setting and/or adjusting values of the user-programmable parameters. In various examples, the user interface 108 may include a graphical user interface (GUI) that allows the user to create and/or edit graphical representations of various neuromodulation waveforms. The GUI may also allow the user to set and/or adjust neuromodulation fields each defined by a set of electrodes through which one or more electrical pulses represented by a waveform are delivered to the patient. The neuromodulation fields may each be further defined by the current fractionalization across the set of electrodes. In various examples, electrical pulses for a stimulation period (such as the duration of a therapy session) may be delivered to multiple neuromodulation fields.

In this document, a "user" includes a physician or other clinician or caregiver who treats the patient using the system 100; a "patient" includes a person who receives, or is intended to receive, neurostimulation via the system 100. In various examples, the patient may be allowed to adjust his or her treatment using system 100 to certain extent, such as by adjusting certain therapy parameters and entering feedback and clinical effect information.

Figure 2:
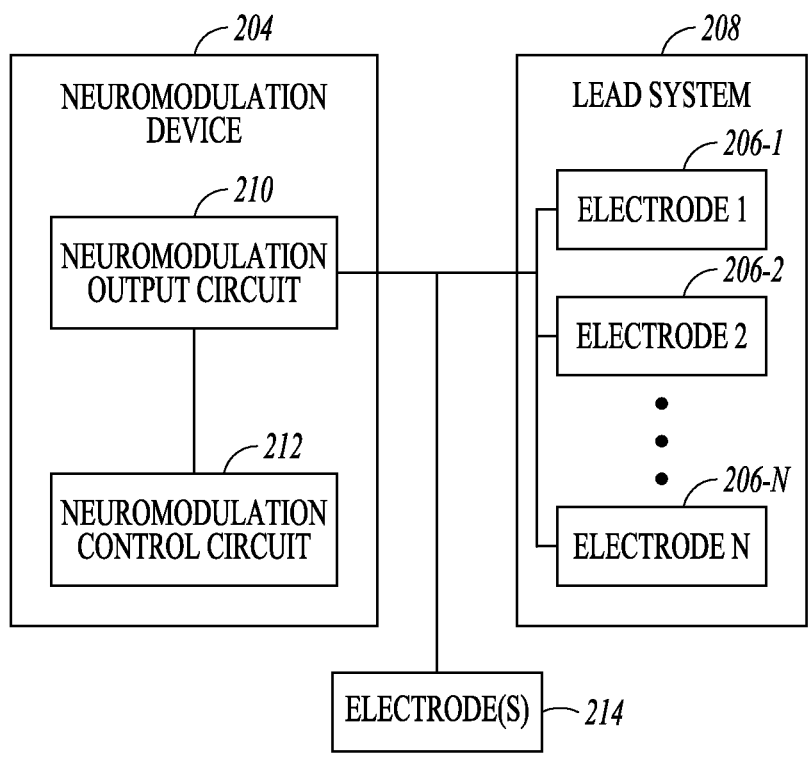
FIG. 2 illustrates, by way of example and not limitation, an embodiment of a stimulation device and a lead system, such as may be implemented in the neuromodulation system.

FIG. 2 illustrates, by way of example and not limitation, an embodiment of a stimulation device 204 and a lead system 208, such as may be implemented in the neuromodulation system 100. The neuromodulation device 204 represents an embodiment of neuromodulation device 104, and includes a neuromodulation output circuit 210 and a neuromodulation control circuit 212. The neuromodulation output circuit 210 may produce and deliver electrical pulses. The neuromodulation control circuit 212 may control the delivery of the electrical pulses from the neuromodulation output circuit 210 according to a plurality of parameters. The lead system 214 includes one or more leads each configured to be electrically connected to neuromodulation device 204 and a plurality of electrodes (including electrode 206-1, 206-2, . . . , 206-N) distributed in the one or more leads. Each of the electrodes has an electrically conductive contact providing for an electrical interface between the neuromodulation output circuit 210 and patient tissue. The number of leads within the lead system, the number of electrodes on the leads, the leady types, and the type of electrodes (e.g. ring, segmented) may vary among the various embodiments.

The electrical pulses may be delivered from the neuromodulation output circuit 212 through a set of electrodes selected from the electrodes 206. In various examples, the electrical pulses may include one or more individually defined pulses, and the set of electrodes may be individually definable by the user for each of the individually defined pulses or each of collections of pulse intended to be delivered using the same combination of electrodes. In various examples, one or more additional electrodes 214 (referred to as reference electrodes) may be electrically connected to the neuromodulation device 204, such as one or more electrodes each being a portion of or otherwise incorporated onto a housing of the neuromodulation device 204. Electrodes on the housing may be referred to as "can electrodes". The neuromodulation may be delivered as a unipolar, bipolar, or multipolar stimulation. Monopolar stimulation uses a monopolar electrode configuration with one or more electrodes selected from the electrodes within the lead system 208 and at least one electrode from electrode(s) 214. Bipolar stimulation uses a bipolar electrode configuration with two electrodes selected from the electrodes within the lead system 208 and none of the electrode(s) 214. The bipolar stimulation may include balanced or unbalanced bipolar mode using a pair of electrodes on a lead, with the balancing current being applied to a reference electrode. Some bipolar stimulation may approximate a monopolar field, and thus may be considered to be a substantially monopolar field or a pseudo-monopolar field. By way of example and not limitation, a first electrode E1 may contribute 100% of the positive current, a second electrode E2 may contribute a small percentage of the negative current (e.g. <5%), and the can may contribute a large percentage of the negative current (e.g. >95%). A substantially monopolar field may be characterized as a field having a can contributing a threshold indicating a relatively high percentage of the current for a given polarity. For example, the threshold may be 75% or may be a percentage between 75% and 100%. Multipolar stimulation uses a multipolar electrode configuration with multiple (two or more) electrodes selected from electrodes within the lead system 208 and none of electrode(s) 214.

Figure 3:
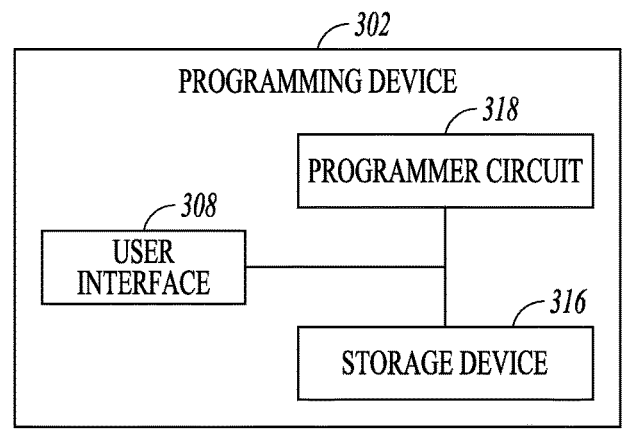
FIG. 3 illustrates, by way of example and not limitation, a programming device, which may be an embodiment of the programming device and implemented in neuromodulation system.

FIG. 3 illustrates, by way of example and not limitation, a programming device 302, which may be an embodiment of the programming device 102 and implemented in neuromodulation system 100. The programming device 302 may include a storage device 316, a programmer circuit 318, and a user interface 308. The programmer circuit 318 may be a part of control circuitry of the programming device 302, and is configured to support one or more functions allowing for programming of neuromodulation devices, such as neuromodulation device 104 including its various embodiments as discussed in this document. In various examples, the programmer circuit 318 may generate a plurality of neuromodulation parameters, collectively referred to as a neuromodulation configuration or neuromodulator settings, that control the delivery of the electrical pulses. In various examples, the neuromodulation configuration may specify a stimulation current (e.g., amplitude or energy of the stimulation) and an electrical current fractionalization across the plurality of electrodes. In some examples, the neuromodulation configuration may include a stimulation location and a stimulation current that corresponds to a metric value. In various examples, the neuromodulation configuration may include a virtual electrode state that specifies a virtual electrode type, location of the virtual electrode in a coordinate space, and stimulation current associated with virtual electrode voltage field and virtual electrode location. Electrical current fractionalization across a plurality of electrodes may be determined based on the voltage field of the virtual electrode.

The storage device 316 may store information used by the programmer circuit 318, including the neuromodulation configuration. The user interface 308 represents an embodiment of user interface 108, and may be coupled to the programmer circuit 318. In various examples, the user interface 308 may allow for definition of a pattern of electrical pulses for delivery during a neuromodulation therapy session by creating and/or adjusting one or more waveforms using a graphical method. The definition may also include definition of one or more neuromodulation fields each associated with one or more pulses in the pattern of electrical pulses. In various examples, the user interface 308 may include a GUI that allows the user to define the pattern pulses and perform other functions using graphical methods.

The circuits or subcircuits included in the neuromodulation system or devices, and their variations discussed in this document, may be implemented using a combination of hardware and software. For example, the circuits may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
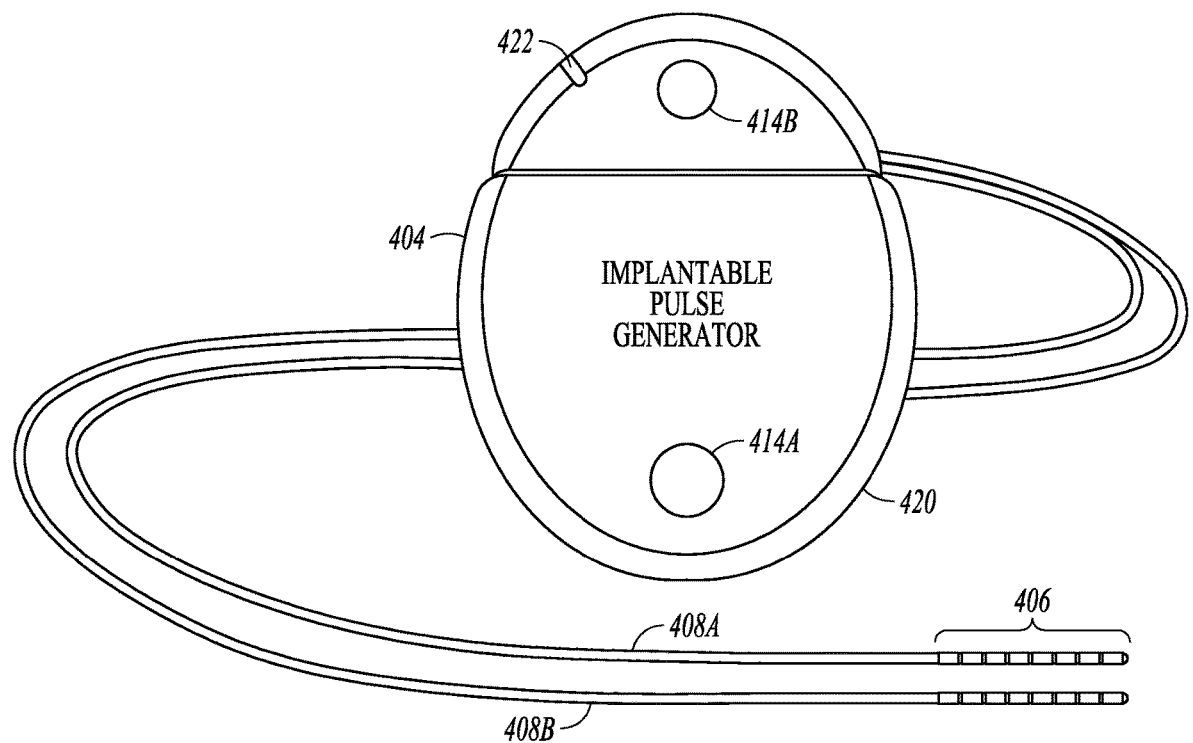
FIG. 4 illustrates, by way of example and not limitation, an embodiment of an implantable pulse generator (IPG) and an implantable lead system.

FIG. 4 illustrates, by way of example and not limitation, an embodiment of an implantable pulse generator (IPG) 404 and an implantable lead system, illustrated as two leads 408A and 408B. The IPG 404 represents an example implementation of neuromodulation device 204, and may include a hermetically-sealed IPG case 420 to house the electronic circuitry of IPG 404. The IPG 404 may include an electrode 414A and may include electrode 414B formed on the IPG case 420. The IPG 404 may include an IPG header 422 for coupling the proximal ends of leads 408A and 408B. Electrodes 426 and/or 428 may each be referred to as a reference electrode or can electrode. The IPG 404 may be communicatively coupled to a programming device, such as the programmer device 102 or the programming device 302, and configured to generate and deliver neuromodulation energy according to the neuromodulator configuration generated by the programming device 102 or 302.

The illustrated lead system includes, by way of example and not limitation, two implantable leads 408A and 408B. As illustrated in FIG. 4A, the IPG 404 may be coupled to the implantable leads 408A-B at a proximal end of each lead. The distal end of each lead includes electrical contacts or electrodes 406 for contacting a tissue site targeted for electrical neuromodulation. In various examples, one or more of the electrodes 406 may be column electrodes (also known as ring electrodes), or segmented electrodes circumferentially disposed on a directional lead such as 408A or 408B.

The implantable leads and electrodes may be shaped and sized to provide electrical neuromodulation energy to a neural target, such as a brain, a nerve target of a spinal cord, or a peripheral nerve target. Neuromodulation energy may be delivered in a unipolar mode between an electrode selected from electrodes 406 and another electrode selected from electrodes 414A and 414B, or in a balanced or unbalanced bipolar mode using a pair, or more, of electrodes on the same lead (e.g., lead 408A or lead 408B), with the balancing current being applied to reference electrodes 414A or 414B. Neuromodulation energy may be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 may include a control circuit that controls delivery of the neuromodulator energy. The control circuit may include a microprocessor, a digital signal processor, application specific integrated circuit (ASIC), or other type of processor, interpreting or executing instructions included in software or firmware. The neuromodulation energy may be delivered according to specified (e.g., programmed) modulation parameters. Examples of setting modulation parameters may include, among other things, selecting the electrodes or electrode combinations used in the neuromodulation, configuring an electrode or electrodes as the anode or the cathode for the neuromodulation, and specifying pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

The modulation parameters may additionally include fractionalization across electrodes. The fractionalization specifies distribution (e.g., the percentage) of the neuromodulation current, voltage, or electrical energy provided by an electrode or electrode combination, which affect the spatial distribution of the resultant neuromodulation field. In an example, current fractionalization specifies percentage cathodic current, percentage anodic current, or off (no current allocation). Current may be fractionalized across the active electrodes, such that active electrodes may receive a respective current percentage. Non-active electrodes are "off" or contribute no current to the neuromodulation. In the monopolar case, the fractionalized currents across the active electrodes add up to 100%. In the bipolar or multipolar cases, the fractionalized currents for at least one polarity add up to 100%, with any remaining percentage being allocated to the reference electrodes. Control of the current in terms of percentage allows precise and consistent distribution of the current among the electrodes even as the overall current amplitude for the parameter set is adjusted. In some examples, the current fractionalization may be defined by assigning an absolute current value (e.g., in milliampere, or mA) rather than a percentage to each electrode. Control of the current in terms of absolute values allows precise dosing of current through each specific electrode. It is suited for changing the current one contact at a time (and allows the user to do so) to shape the neuromodulation like a piece of clay (pushing/pulling one spot at a time).

The current fractionalization takes into account electrode/tissue coupling differences, which are the differences in how the tissue underlying each electrode reacts to electrical neuromodulation. In addition, electrodes on the distal portion of the lead may have lower gradient in the longitudinal direction, as electrical field strength may taper down at the ends of the lead. Current fractionalization may accommodate variation in the tissue underlying those electrodes. Various embodiments described herein implement a programmed algorithm to determine the appropriate fractionalization to achieve a desired neuromodulation field property.

Figure 5:
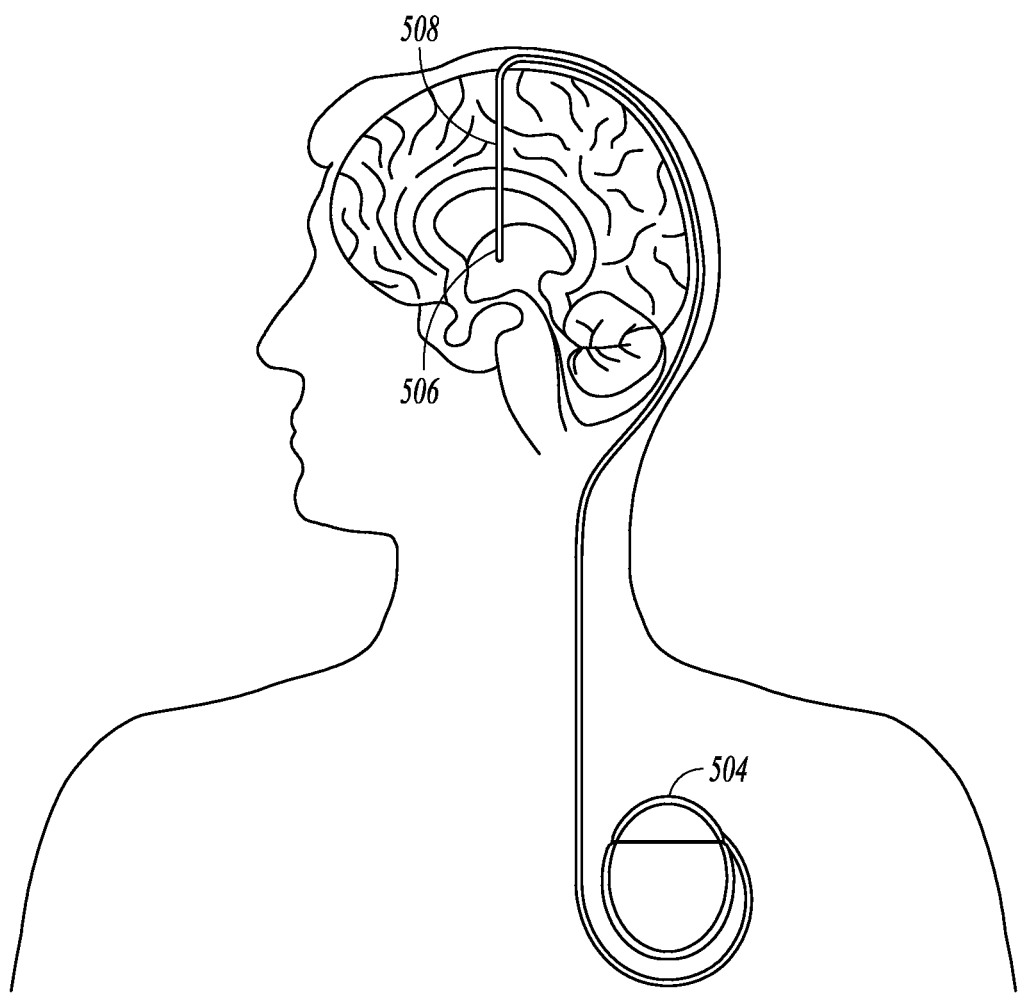
FIG. 5 illustrates, by way of example and not limitation, an embodiment of an IPG and an implantable lead system arranged to provide brain neuromodulation to a patient.

FIG. 5 illustrates, by way of example and not limitation, an embodiment of an IPG 504 and an implantable lead system 508 arranged to provide brain neuromodulation to a patient. An example of IPG 504 includes the IPG 404. The lead system 508 may include electrodes 506. An example of lead system 508 includes one or more of the leads 408A-B. An example of the electrodes 506 includes at least a portion of the electrodes 406. In the illustrated example, the IPG 504 and the implantable lead system 508 may provide DBS to a patient, with the neuromodulation target being neuronal tissue in a subdivision of the thalamus of the patient's brain. Other examples of DBS targets include neuronal tissue of the globus pallidus (GPi), the subthalamic nucleus (STN), the pedunculopontine nucleus (PPN), substantia nigra pars reticulate (SNr), cortex, globus pallidus externus (GPe), medial forebrain bundle (MFB), periaquaductal gray (PAG), periventricular gray (PVG), habenula, subgenual cingulate, ventral intermediate nucleus (VIM), anterior nucleus (AN), other nuclei of the thalamus, zona incerta, ventral capsule, ventral striatum, nucleus accumbens, white matter tracts connecting these and other structures. The DBS targets may also include regions determined analytically based on side effects or benefits observed in one or more patients, as well as regions specified by the user.

Figure 6:
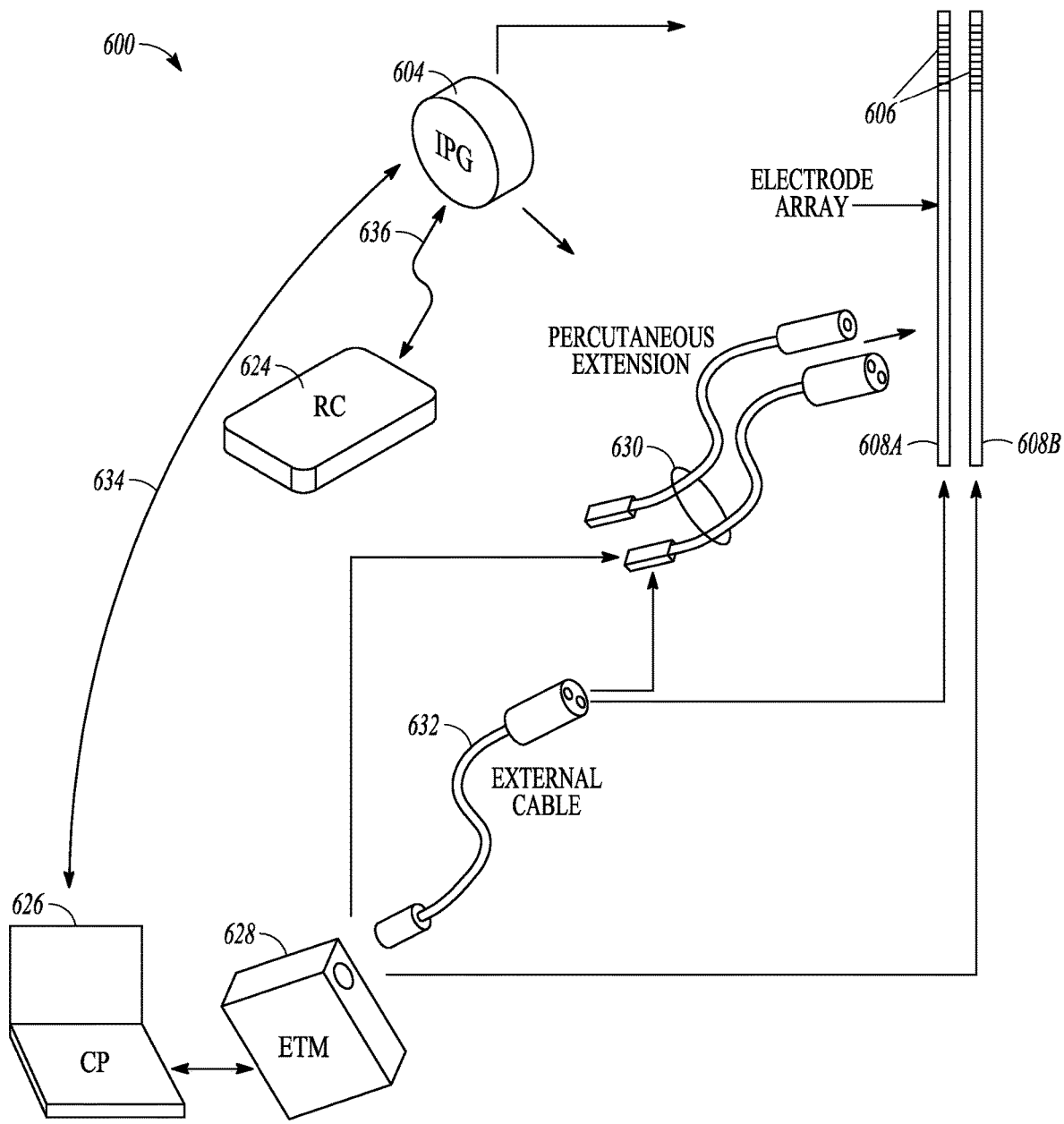
FIG. 6 illustrates, by way of example and not limitation, an embodiment of portions of a neuromodulation system.

FIG. 6 illustrates, by way of example and not limitation, an embodiment of portions of a neuromodulation system 600. The system 600 includes an IPG 604, implantable neuromodulation leads 608A and 608B, an external remote controller (RC) 624, a clinician's programmer (CP) 626, and an external trial modulator (ETM) 628. The system 600 may additionally include external sensors configured to sense one or more physiological parameters, such as a heart rate sensor, a pulse oximeter, an electrocardiogram sensor, an inertial sensor, or an electroencephalogram sensor, among others. The IPG 604 may be electrically coupled to the leads 608A and 608B directly or through percutaneous extension leads 630. The ETM 634 may be electrically connectable to the leads 608A and 608B via one or both of the percutaneous extension leads 630 and/or the external cable 632. The system 600 represents an embodiment of system 100, with IPG 604 representing an embodiment of the neuromodulation device 104, electrodes 606 of leads 608A and 608B representing the electrodes 106, and CP 626, RC 624, and the ETM 628 collectively representing the programming device 102.

The ETM 628 may be standalone or incorporated into the CP 630. The ETM 628 may have similar pulse generation circuitry as IPG 604 to deliver neuromodulation energy according to specified modulation parameters as discussed above. In an example, the ETM 628 is an external device and may be used as a preliminary stimulator after leads 408A and 408B have been implanted and used prior to stimulation with IPG 604 to test the patient's responsiveness to the stimulation that is to be provided by IPG 604. An external ETM 634 may be more easily configurable than the IPG 604.

The CP 626 may configure the neuromodulation provided by the ETM 628. If the ETM 628 is not integrated into the CP 626, then the CP 626 may communicate with ETM 628 using a wired connection (e.g., over a USB link) or by wireless telemetry such as using a wireless communications link. The CP 626 may also communicate with IPG 604 using a wireless communications link 634.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. The IPG 604 may include the first coil and a communication circuit. The CP 626 may include or be otherwise electrically connected to the second coil such as in the form of a wand that may be place near the IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of r=λ/2π, where λ is the wavelength of the transmitted electromagnetic energy. In one example, a communication range of an RF telemetry link is at least six feet but may be as long as allowed by the particular communication technology. RF antennas may be included, for example, in the header of the IPG 604 and in the housing of the CP 630, eliminating the need for a wand or other means of inductive coupling. An example is such an RF telemetry link is a Bluetooth® wireless link.

The CP 626 may be used to set modulation parameters for the neuromodulation after the IPG 604 has been implanted. This allows the neuromodulation to be tuned if the requirements for the neuromodulation change after implantation. The CP 626 may also upload information from or download information to the IPG 604.

The RC 624 also communicates with the IPG 604 using a wireless link 636. The RC 624 may be a communication device used by the user or given to the patient. The RC 624 may have reduced programming capability compared to the CP 626. This allows the user or patient to alter the neuromodulation therapy but does not allow the patient full control over the therapy. For example, the patient may be able to increase the amplitude of neuromodulation pulses or change the time that a preprogrammed stimulation pulse train is applied. The RC 624 may be programmed by the CP 626. The CP 626 may communicate with the RC 624 using a wired or wireless communications link. In some embodiments, the CP 626 is able to program the RC 624 when remotely located from the RC 624. In some examples, the RC 624 may download data to and upload data from the IPG 604.

Figure 7:
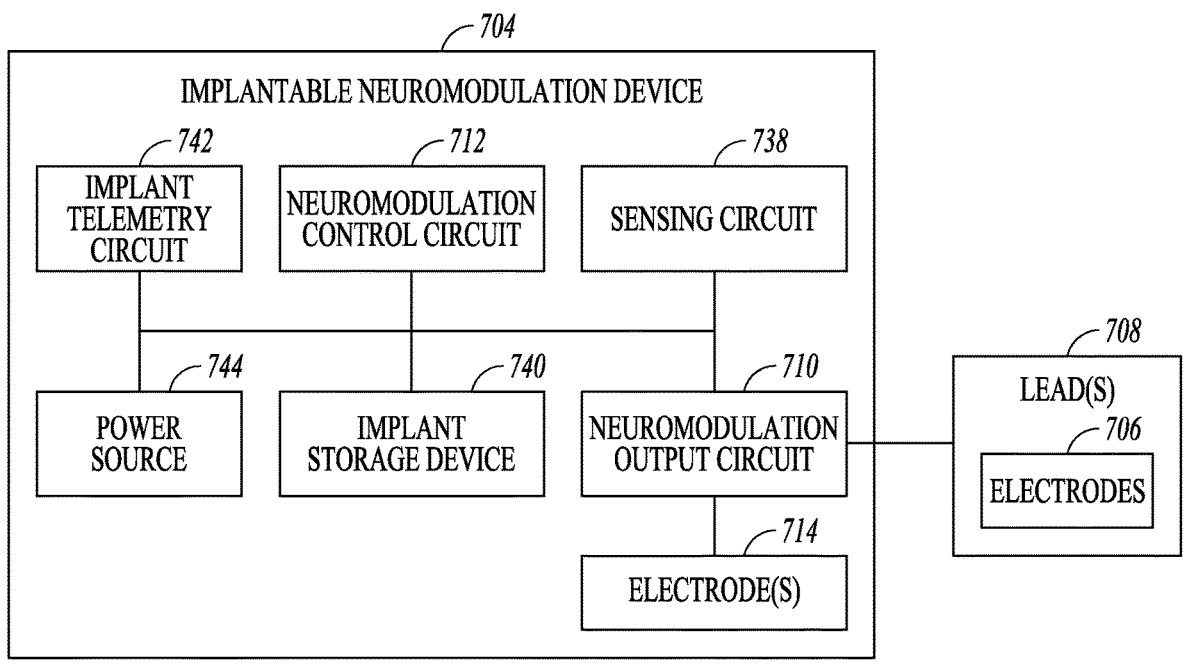
FIG. 7 illustrates, by way of example and not limitation, an embodiment of implantable neuromodulation device and one or more leads of an implantable neuromodulation system, such as the implantable system.

FIG. 7 illustrates, by way of example and not limitation, an embodiment of implantable neuromodulation device 704 and one or more leads 708 of an implantable neuromodulation system, such as the implantable system 600. The implantable neuromodulation device 704 represents an embodiment of stimulation device 104 or 204 and may be implemented, for example, as the IPG 604. Lead(s) 708 represents an embodiment of lead system 208 and may be implemented, for example, as implantable leads 608A-B. The lead(s) 708 includes electrodes 706, which represents an embodiment of electrodes 106 or 206 and may be implemented as electrodes 606. In some examples, the implantable stimulator 704 may additionally be communicatively coupled to one or more external sensors configured to sense one or more physiological parameters, such as a heart rate sensor, a pulse oximeter, an electrocardiogram sensor, an inertial sensor, or an electroencephalogram sensor, among others.

The implantable neuromodulation device 704 may include a sensing circuit 738 when the stimulator needs a sensing capability, neuromodulation output circuit 710, a neuromodulator control circuit 712, an implant storage device 740, an implant telemetry circuit 742, a power source 744, and one or more electrodes 714. The sensing circuit 738, when included, may be configured to sense one or more physiologic signals for purposes of patient monitoring and/or feedback control of the neuromodulation. Examples of the physiologic signals include neural and other signals each indicative of a condition of the patient that is treated by the neuromodulation and/or a response of the patient to the delivery of the neuromodulation. The stimulation output circuit 212 is electrically connected to electrodes 706 through one or more leads 708 as well as electrodes 707, and delivers each of the neuromodulation pulses through a set of electrodes selected from electrodes 706 and electrode(s) 707. The device control circuit 714 represents an embodiment of device control circuit 214, and controls the delivery of the pulses according to the stimulation configuration (including stimulation parameters) received from the programming device 102 or 302. In one embodiment, the device control circuit 714 controls the delivery of the pulses using the one or more sensed physiologic signals. The implant telemetry circuit 744 provides the implantable stimulator 704 with wireless communication with another device, such as the CP 630 or the RC 632, including receiving values of the plurality of stimulation parameters from the other device. The implant storage device 746 stores the received stimulation configuration, including values of the plurality of stimulation parameters. The power source 748 provides the implantable stimulator 704 with energy for its operation. The power source 748 may include a battery. In one embodiment, the power source 748 includes a rechargeable battery and a battery charging circuit for charging the rechargeable battery. The implant telemetry circuit 744 may also function as a power receiver that receives power transmitted from an external device through an inductive couple. The electrode(s) 714 allow for delivery of the pulses in the monopolar mode or unbalanced bipolar mode. Examples of the electrode(s) 714 include electrode 414A and electrode 414B in IPG 404 as illustrated in FIG. 4A.

In an example, the implantable neuromodulation device 704 may be used as a master database. A patient implanted with implantable stimulator 704 (such as may be implemented as IPG 604) may therefore carry patient information needed for his or her medical care when such information is otherwise unavailable. The implant storage device 740 may be configured to store such patient information. For example, the patient may be given a new RC 632 and/or travel to a new clinic where a new CP 630 is used to communicate with the device implanted in him or her. The new RC 632 and/or CP 630 may communicate with the implantable stimulator 704 to retrieve the patient information stored in implant storage device 740 through the implant telemetry circuit 744 and the wireless communication link 640, and allow for any necessary adjustment of the operation of the implantable stimulator 704 based on the retrieved patient information. The patient information be stored in the implant storage device 746 may include, for example, various types of neuromodulation settings. Examples may include positions of lead(s) 708 and electrodes 706 relative to the patient's anatomy (transformation for fusing computerized tomogram (CT) of post-operative lead placement to magnetic resonance imaging (MRI) of the brain), clinical effect data, objective measurements using quantitative assessments of symptoms (e.g., using microelectrode recording, accelerometers, and/or other sensors), and/or other information considered important or useful for providing adequate care for the patient. In various examples, the patient information to be stored in implant storage device 740 may include data transmitted to implantable stimulator 704 for storage as part of the patient information and data acquired by implantable stimulator 704, such as by using sensing circuit 742.

Figure 8:
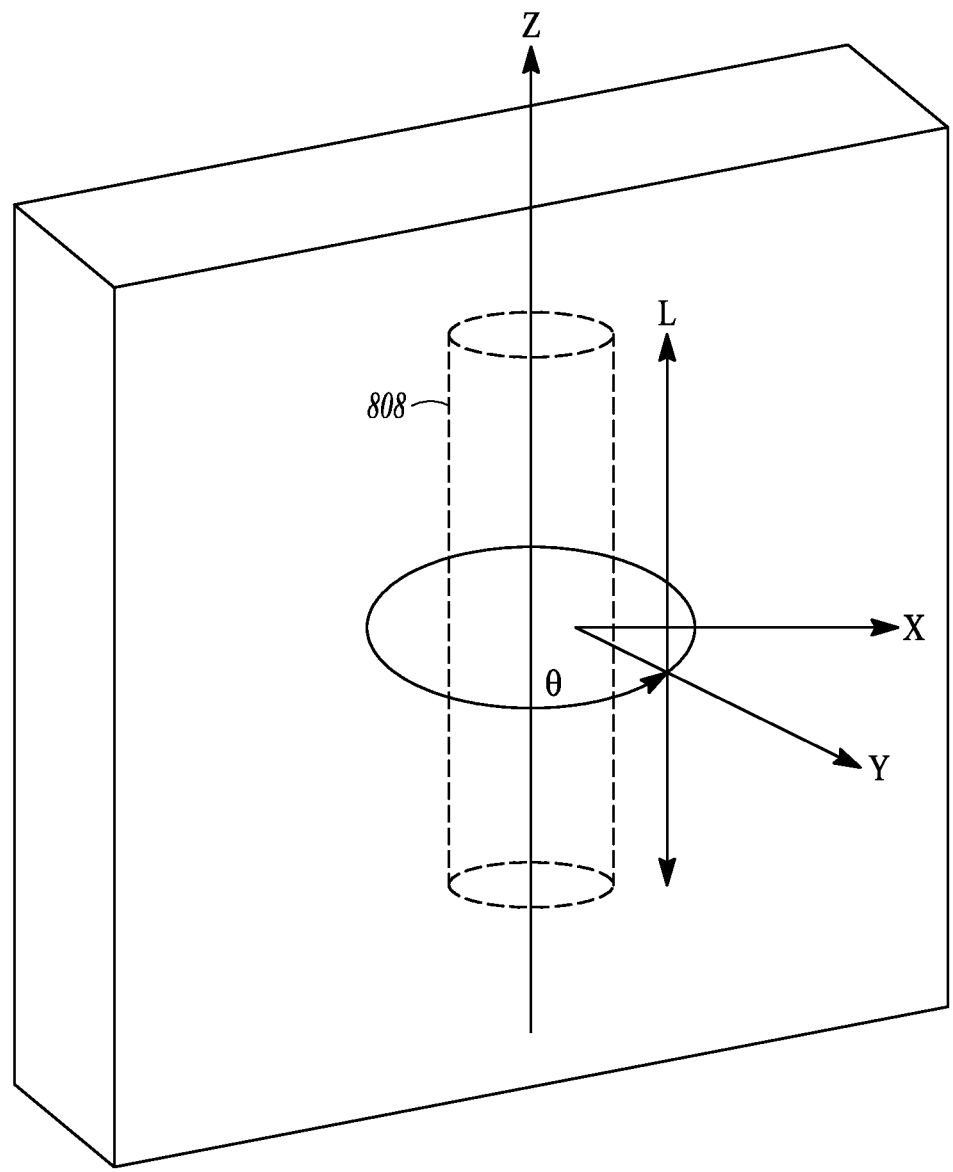
FIG. 8 is a schematic diagram illustrating radial current steering along various electrode levels along the length of the lead.
Figure 9A:
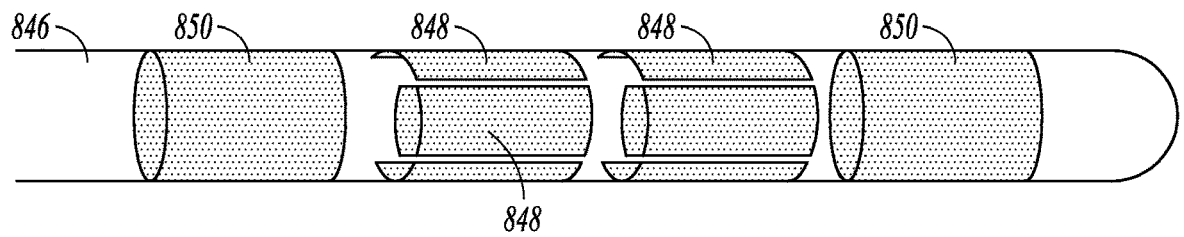
FIGS. 9A-9E illustrate, by way of example, and not limitation, various examples of leads with which radial current steering may be used.
Figure 9B:
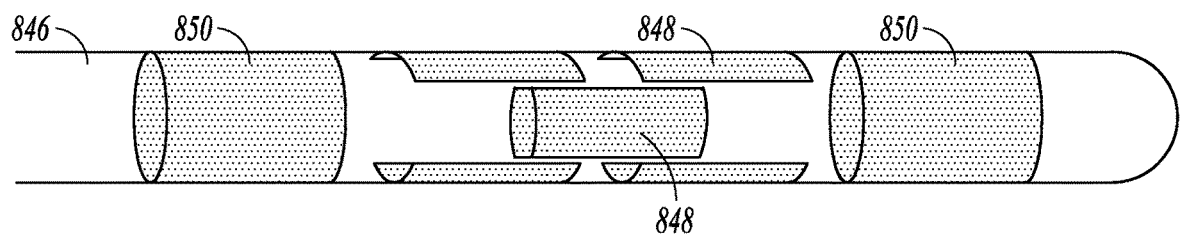
Figure 9C:
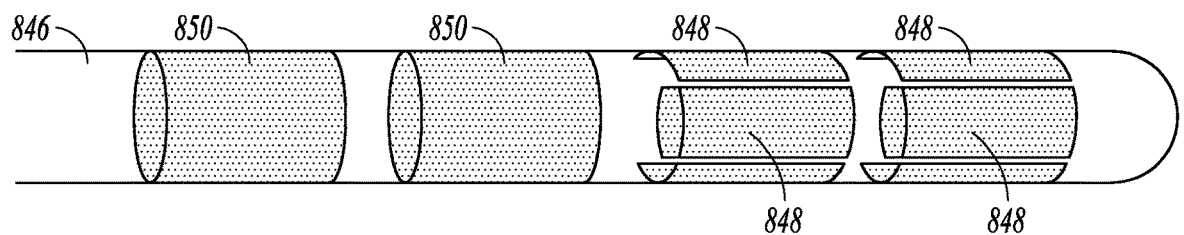
Figure 9D:
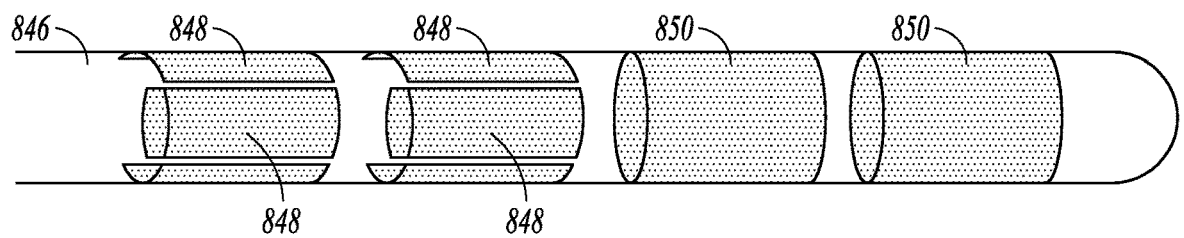
Figure 9E:
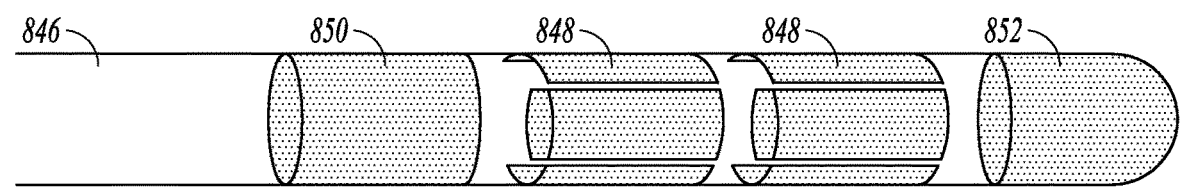

FIG. 8 is a schematic diagram illustrating radial current steering along various electrode levels along the length of the lead 808. The segmented electrode configuration is capable of steering current in the x-axis, y-axis, and z-axis. Radial coordinates may be used including L (a position along the lead axis), r (a distance from the lead axis) and angle θ. Thus, the centroid of stimulation may be steered in any direction in the three-dimensional space surrounding the lead. The stimulation may be shifted at each level along the length L of the lead. The use of multiple sets of segmented electrodes at different levels along the length of the lead allows for three-dimensional current steering. In some embodiments, the sets of segmented electrodes are shifted collectively, and in at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level.

FIGS. 9A-9E illustrate, by way of example, and not limitation, various examples of leads with which radial current steering may be used. The figures illustrate lead bodies 846, segmented electrodes 848 (e.g. 3 electrodes spaced 120° from each other around the lead.) ring electrodes 850, and a tip electrode 852. These figures are not intended to limit the present subject matter to any particular arrangement of electrodes, but are intended to illustrate that these electrode arrangements are capable of having the current distributed over active ones of these electrode to control the shape, size and direction of the modulation field. The current delivered to each of the active electrodes can be independently controlled to provide a very large number of parameter setting options to create modulation fields of many shapes and sizes. Polarity is one of the parameter setting options.

Figure 10:
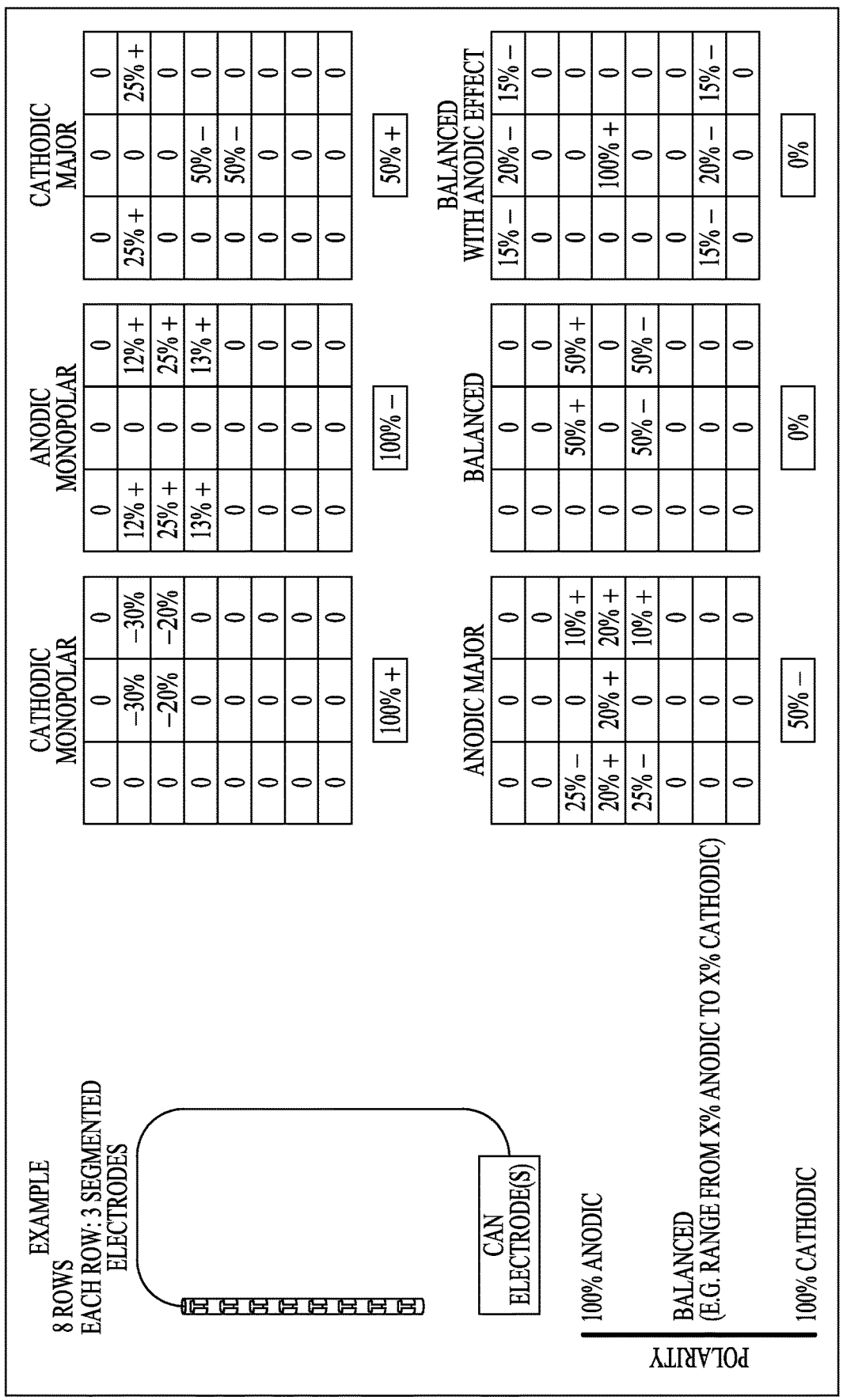
FIG. 10 illustrates examples of fractionalizations to provide different modulation types.

FIG. 10 illustrates examples of fractionalizations to provide different modulation types. The neuromodulation device includes an IPG with a can electrode, and a lead with 8 sets or rows of electrodes, where each set or row includes 3 fractionalized electrodes distributed around the lead (e.g. at 0°, 120° and 240). The figure illustrates six tables that have 8 rows and 3 columns. Each table represents the lead electrodes, such that each cell in the table represents one of the electrodes on lead, and the cell below the table represents a can electrode. The data within the cells is intended to illustrate fractionalization values for the electrodes. The total positive charge (anodic) will equal the total negative charge (cathodic) in the system. However, up to 100% of the anodic or cathodic contribution may be provided by the can electrode. As such, the polarity of the modulation field at the targeted region(s) may be 100% cathodic (conventional monopolar DBS neuromodulation), 100% anodic (anodic monopolar), mostly cathodic (e.g. cathodic major), mostly anodic (anodic major), or balanced such as may occur if there is no current contribution by the can or other reference electrode). It may be possible to provide balanced polarity in so far as the can electrode is not providing a current contribution, but the current contributions for one polarity is spread across many electrodes and the current contributions for the other polarity is provided by one or a few electrodes. Thus, it may be possible to provide a balanced modulation using the lead electrodes, but still provide an anodic effect for a particular targeted region.

The polarity of the modulation field at the lead electrodes (illustrated by the values within the table cells) may be 100% anodic (no cathodic contribution), 100% cathodic (no anodic contribution), balanced (anodic contribution equals cathodic contribution), approximately or nearly balanced (anodic contribution is within +/−X % of cathodic contribution; such as 45%:50% or 50%:45% if X=5). To be characterized as relatively balanced, a relatively small percentage (X % where X=10 or less by way of example) of the cathodic or anodic contribution may be provided by the can electrode. As identifier earlier, the polarity of the field may also be considered substantially monopolar or pseudo-monopolar if the can is contributing a relatively larger percentage of the current (e.g. 90% or higher). The present subject matter is not limited to these values, as the system is capable of using the lead electrodes to provide anywhere from 0 to 100% of the total anodic energy, or using the lead electrodes to provide anywhere from 0 to 100% of the total cathodic energy. If something is anodic major, the anodic contribution of the lead electrodes sums to 100%, but the cathodic contribution of the lead electrodes sums to less than 100%. Similarly, cathodic major indicates that the cathodic contribution of the lead electrodes sums to 100%, but the anodic contribution of the lead electrodes sums to less than 100%.

These fractionalizations and stimulation type may be stored as neuromodulation settings for a programmed neuromodulation therapy. Other information that may be stored as neuromodulation parameter settings may include clinical effects, targeted region(s), and avoidance region(s), if any, to particular neuromodulation parameter settings (e.g. amplitude, pulse width, fractionalization, polarity).

Figure 11:
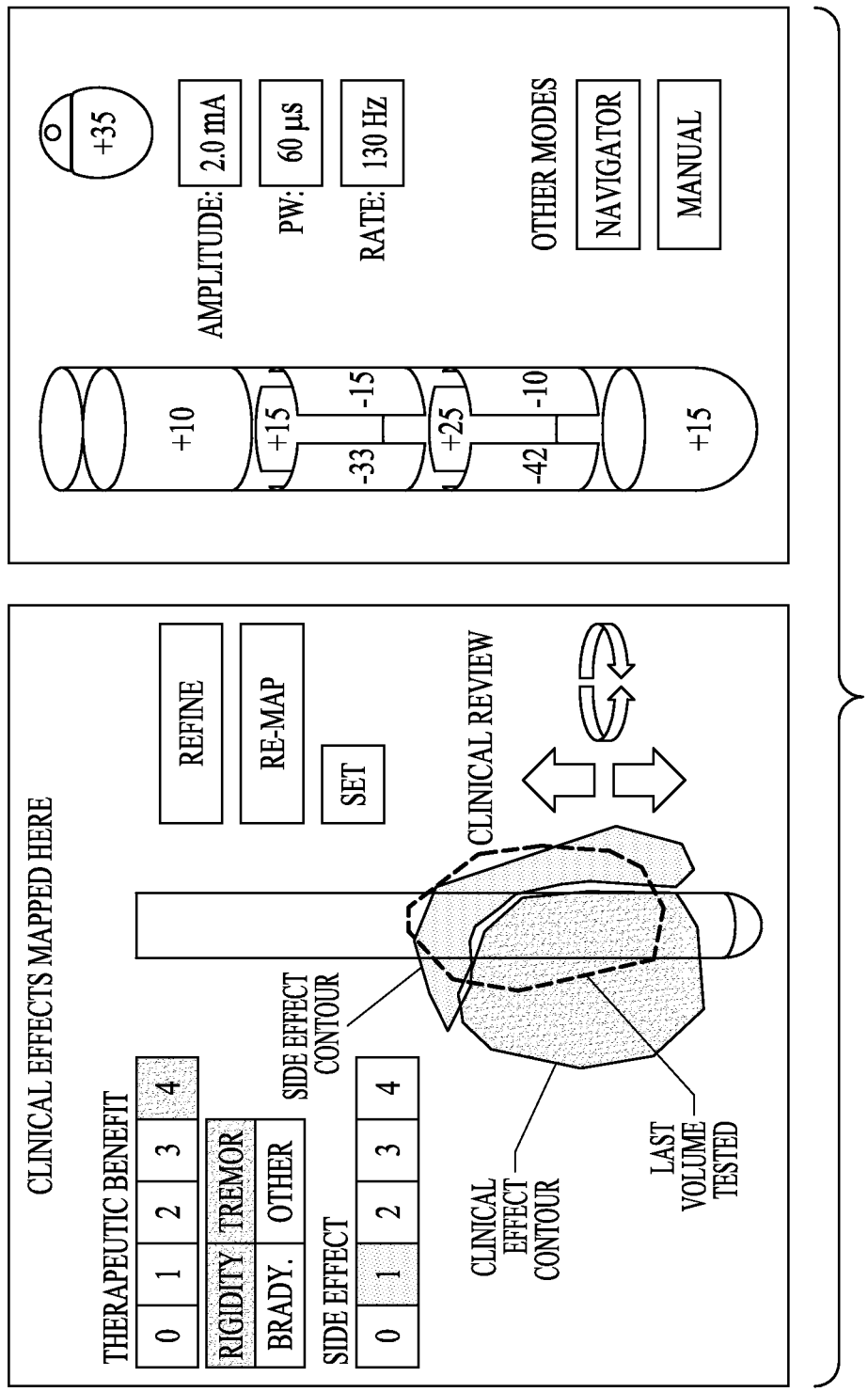
FIG. 11 illustrates an example of a presentation of clinical effects and stimulation configuration on a user interface.

FIG. 11 illustrates an example of a presentation of clinical effects and stimulation configuration on a user interface. The target volume and the one or more clinical effects may be presented, along with a stimulation configuration (e.g. polarity and fractionalization, and stimulation pulse parameters including amplitude, width, and frequency). A "Navigator" button can open a navigation console that allows the user to navigate predefined stimulation configurations and select a predefined stimulation configuration. A "Manual" button can open a manual programming console that allows the user to manually define a stimulation configuration.

After the target volume is determined, stimulation configuration circuitry 962 can automatically generate the stimulation configuration for activating a volume of tissue substantially matching the target volume. An inverse modeling algorithm may be used to automatically generate the stimulation configuration for activating a volume of tissue in the patient that substantially matches the target volume. The target volume can be defined and refined by one or more iterations using the one or more clinical effects resulting from the test volume used in each iteration. For example, a test volume may be generated, where the test volume would from delivery of neuromodulation using the stimulation configuration. Alternatively, a test volume can be specified, and the inverse modeling algorithm can be used to automatically generate the stimulation configuration for activating that test volume. In one embodiment, the inverse modeling algorithm relates a stimulation configuration to a volume of activation ("VOA"). VOA designates an estimated region of tissue that will be stimulated for a particular set of stimulation parameters. The terms "stimulation field map" (SFM) also refer to the VOA This VOA may be referred to as a stimulation field model (SFM). Thus, for a given polarity, pulse width, frequency, fractionalization, the field and tissue modeling information can determine the current required to activate a volume of tissue (e.g. threshold current). This information may be used to create a SFM. The stimulation configuration can be generated using a library including data mapping volumes of activation to stimulation configurations and/or using an analytical derivation of the stimulation configuration that generates the stimulation volume.

In various embodiments, the system can determine the one or more clinical effects and/or present the one or more clinical effects using information entered by the user, information entered by the patient, and/or signals sensed from the patient. The clinical effects can include those represented by one or more types of therapeutic benefits and one or more types of side effects. A therapeutic benefit score representative of a degree of the one or more therapeutic benefits (0 for no therapeutic benefit, 4 for highest degree of therapeutic benefit), and a side effect score representative of a degree of the one or more side effects (0 for no side effect, 4 for highest degree of side effect), may be presented. The clinical effects may be presented as a therapeutic benefits contour which is indicative of a volume of the tissue excitable for one or more desirable therapeutic benefits, and a side effect contour which is indicative of a volume of the tissue excitable for one or more unwanted side effects.

To estimate or determine a SFM, the electric field arising from the electrical energy delivered according to the stimulation parameters may be determined or modeled, and then the tissue response to an electrical field may be determined or modeled. The modeling for the electric field and the tissue response can be used to estimate or determine the SFM. Electric fields may be modeled in a variety of ways, including but not limited to a finite element analysis model. Tissue responses may also be modeled in a variety of ways, including but not limited to a neural element model or axon model or some estimator that calculates features of the electric field and uses them to determine the current threshold required to induce a response.

Figure 12:
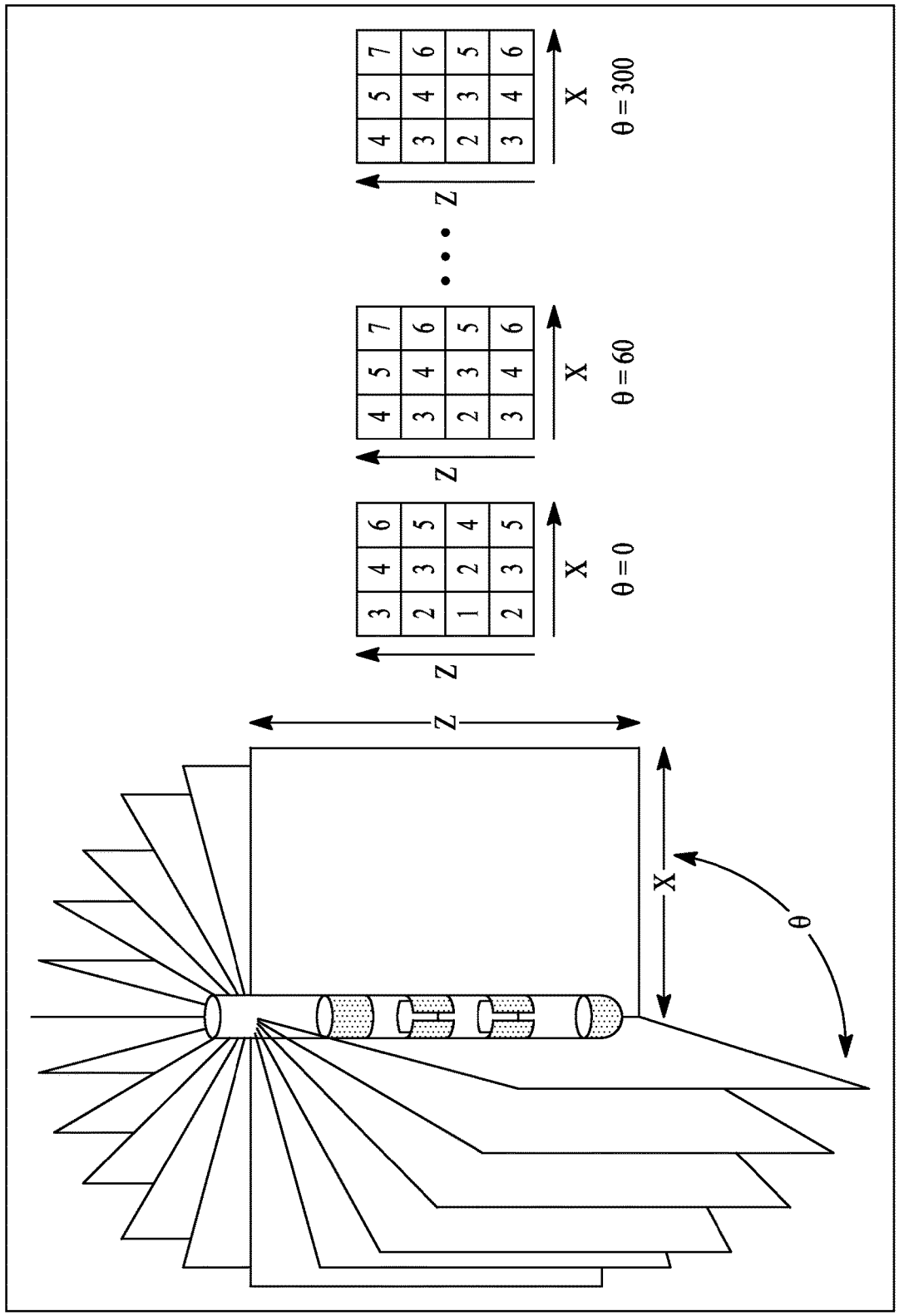
FIG. 12 illustrates a series of planes distributed around a lead having electrodes and threshold tables (e.g. $I_{th}$ tables) for those planes.

FIG. 12 illustrates a series of planes distributed around a lead having electrodes and threshold tables for those planes. The information (e.g. SFM) based on the electric field model and tissue response model can be used to produce planar distributions of stimulation threshold values for these planes. These stimulation threshold values may be dependent on other stimulation parameters, such as stimulation duration (for example, pulse width), stimulation frequency, and the like. Each of the planes can be divided into multiple regions (for example, squares or rectangles) with an associated stimulation threshold value (such as a threshold current or voltage) which, when applied to the lead will activate or stimulate the tissue at that region, as illustrated in FIG. 12. By way of example, the stimulation threshold value may be a threshold current ($I_{th}$). However, a threshold voltage or other electrical characteristic may be used to identify the stimulation threshold value. The radial coordinates x, z and θ may be used to uniquely identify a particular region of a particular plane. The x-value corresponds to a radial distance from the lead. The z-value corresponds to an axial coordinate along the longitudinal axis of the lead. The θ-value corresponds to the relative angle of the plane in which the region resides. Thus, the $I_{th}$ values can be stored in a database as a series of $I_{th}$ tables, $I_{th}$ (z, x, θ), which can also be indexed relative to other state variables, as described below. A visual example of these $I_{th}$ tables is presented in FIG. 12 where each plane (identifiable by θ) represents one of the tables. The illustrated $I_{th}$ tables are simple tables. As the characterized regions on each of the planes gets smaller, the number of $I_{th}$ values gets larger. Also, as the threshold current is affected by polarity, pulse width, frequency, fractionalization and other pulse parameters, the data elements in the database of Ith values may be specific to the various combinations of polarity, pulse width, frequency, fractionalization and the other pulse parameters.

The neuromodulation programming may involve steering the field through space around the lead. An example of a steering parameter is "rotation" which represents the angular direction of the field extending away from the lead. Another example of a steering parameter is "spread" which relates to the angular spread of the field around the circumference of the lead. In addition to rotation and spread, the stimulation (e.g., stimulation current) can be steered to different positions and arrangements around the lead using "axial position" in z direction. The system may be configured to convert these steering parameters (z, spread, rotation) into current fractionalization parameters for the electrodes on the lead.

The large database of $I_{th}$ values can be compressed using a variety of lossless or lossy techniques. Examples of lossless compression involves the recognition that many fractionalization states are not unique or available, and the recognition of symmetry and redundancy in the data. The database can be reduced to a set of unique $I_{th}$ tables and a map which relates the Ith tables to the different fractionalizations (i.e., the different axial position, rotation, and spread values) and, optionally, to different pulse widths or frequencies. Lossy compression may approximate Ith tables that are determined to be sufficiently similar to the original table. Another lossy compression method may use MPEG compression or a similar process that generates data describing differences in the data.

The regions of space for which $I_{th}$ values are determined may be represented using "voxels". A voxel represents a volumetric element of a computerized physiologic structure or analytically determined structure, such as a computerized tissue representation, in a 3D space. A voxel may have specified size in each dimension, such as 0.5 mm or less. The 3D voxelized model may include a computer-generated graphic model representing volumetric tissue elements and their responses to the electrostimulation. In an example, the 3D voxelized model comprises an array of 3D voxels each specified as belonging to one of a plurality of physiologic structures, such as a target region or an avoidance region. A target region may refer to a physiologic structure, analytically derived or user selected regions (e.g., of the brain or other areas), or combinations thereof. The target region may be associated with known therapeutic benefits of the electrostimulation. An avoidance region may refer to a physiologic structure, analytically derived or user selected regions, or combinations thereof that are associated with a known side effect of the electrostimulation. Each target or avoidance region may be assigned a corresponding weight factor w correlated to a clinical outcome of electrostimulation delivered at respective physiologic structures, such as a therapeutic benefit or a side effect. For example, a target region ($S^+$) may be associated with a positive weight factor, and an avoidance region ($S^-$) may be associated with a negative weight factor. The absolute value of the weight factor signifies relative significance of the clinical outcome. In an example of DBS, an avoidance structure that produces a slight slur (a side effect of DBS) may be of less clinical significance or importance than an avoidance structure that causes seizure (another side effect of DBS). As such, a weight factor with a larger absolute value may be assigned to the seizure-causing structure. A user may assign or adjust weight factors for various regions based on known clinical effects of the electrostimulation on the respective regions.

Each of the 3D voxels of the received 3D voxelized model has a voxel volume and a voxel value. The voxel volume represents a geometric size of the voxel. The voxel value may, among other possibilities, represent a likelihood that the corresponding voxel volume may contribute to the clinical outcome (therapeutic benefit or side effect). For example, a voxel value of 0.8 indicates that the voxel has 80% chance of having the benefit or side effect of the structure to which it is a part. In another example, multiple regions could be represented in the same structure of voxels, where the voxel values represent the relative weights of the various regions (e.g., the slur versus the seizure inducing regions). Each set of voxels may either belong to the target regions (with therapeutically beneficial effects) or avoidance regions (with side effects). In yet another example, all regions, including both the target and avoidance regions, may be represented in the same set of voxels, in which case all the voxels in the avoidance region are assigned negative voxel values, and all the target voxels are assigned positive voxel values. In an example, a user may adjust one or more of the weight factors w associated with various target structures and avoidance structures, the voxel volumes, or the voxel values associated with the 3D voxels.

The 3D voxelized model, along with the voxel volumes and the voxel values associated with the 3D voxels, may be used to determine a metric value. A preprocessing step may translate the target and side effect regions, which are in "patient space" into "lead space". The patient space may be coordinate system based on the imagery of the patients head. Lead space may be a coordinate system that has (x=0,y=0; z=0) at the center of the lead at the distal edge of the distal row of electrodes. Increasing z is up the lead towards the proximal end. The x axis goes through the center of electrode 2 (for all lead types), and the y axis is the cross product of the z and x axes. The system may determine, for each of the regions, a respective metric value (MV) using the received 3D voxelized model. The MV represents a clinical effect of electrostimulation on the tissue according to a stimulation current and fractionalization of electrical current. In an example, the MV may be computed using a weighted combination of the volumes of the array of 3D voxels in the voxelized model. For example, for each 3D voxel i in a region j (either a target region or an avoidance region), a corresponding voxel effect (X(i, j)) representing voxel i's contribution to the MV for the region j, may be computed using the following equation:

$$X(i,j) = \text{vol}(j) * w(j) * \text{val}(i,j) \quad (1)$$

where vol(j) represents the voxel volume for each voxel in region j, and w(j) represents the weight factor associated with the region to which the voxel i belongs (region j in this case), and val(i, j) represents the voxel value for voxel i in region j. All the voxels in a particular region (e.g., region j) have the same voxel volume (vol(j)), and all the voxels in a particular region (e.g., region j) share the same weight (w(j)) of that region. When there is one 3D matrix of voxels that contains both target and side effect voxels, the voxel-specific weight factor w(i, j) is a positive scalar if the 3D voxel i is situated in a target region, or a negative scale if the 3D voxel i is situated in an avoidance region. In the general case, the voxel values are always positive, and the weight of the region is positive for target regions and negative for side effect regions Therefore, the 3D voxels situated in a target region ($S^+$) have positive voxel effects X, and the 3D voxels situated in an avoidance region ($S^-$) have negative voxel effects X. The absolute value of the weight factor represents relative significance of the clinical outcome. In an example, the weight factor is a non-zero scalar between −1 and 1. In general, the target region has a weight of 1 and the side effect regions have any negative value. The magnitude of the side effect regions weight gives the relative importance assigned to the side effect. A range for side effect weights may be 0>weight>=−100. If the weight is zero, it has no importance. If the weight is −100, that means stimulating a voxel volume of it can wipe out the benefit of 100 times that volume of target voxels The MV for the region j may be determined using a combination of voxel effects across all N voxels within the region j in the 3D voxelized model that have been stimulated, according to the following Equation:

$$MV = X(1,j) + X(2,j) + \ldots + X(N,j) \quad (2)$$

Associated with the MV is a stimulation current (Is) applied to the 3D voxels in the region. The MV may also be associated with electrical current fractionalization ($F_I$) across a plurality of electrodes that deliver stimulation energy to the region. The relationship among Is, $F_I$, and the MV may be represented as: Is=$f$(MV, $F_I$), where $f$ is a linear or nonlinear function. The MV represents a clinical outcome with tissue recruitment from a physiologic or analytically determined region. The tissue recruitment may be represented by the number of 3D voxels recruited and their respective voxel effect X(i, j).

The system may determine a stimulation configuration corresponding to a best metric value ($MV_{opt}$) that satisfies a specific optimization condition. In an example, $MV_{opt}$ may be identified as a metric value that exceeds a threshold metric value $MV_{TH}$. In another example, $MV_{opt}$ may be identified as the largest MV under a specific electrical current fractionalization $F_I$. According to the relationship (Is, MV)=function of (Fi, PW, X), where X is the overall list of voxel metric effects, or X=function of (Target & weight, Avoidance regions & weights). The fractionalization and pulse width determine the Ith table to be used. The target and weight and side effects and weights determine the effect each voxel has on the metric. There may be an avoidance volume that includes all of the volume of the patient's head and has some usually much lower weight. The purpose of this avoidance volume is to keep the amplitude as low as is feasible, as any increase in amplitude adds the additional cost of that volume of tissue. Combining the Ith and the metric contribution of each voxels gives a metric effect of each change in amplitude. Summing along the list of metric changes by amplitude gives the amplitude that produces the best metric value. There may be more than one amplitude that produce the best metric value, and the lowest amplitude with the metric value is used. The inputs may include the fractionalization and pulse width, and the target and avoidance regions and their weights. The output may include the best metric value and the amplitude that had the best metric value. The system may iterate over fractionalizations to find the one with best metric value. That fractionalization and the lowest amplitude associated with that metric value are returned as discussed above, associated with the $MV_{opt}$ (e.g., a maximum MV under the specific electrical current fractionalization $F_I$) is a corresponding Is. In an example, the stimulation configuration generator circuit 824 may determine a minimal stimulation current ($I_{min}$) that results in an $MV_{opt}$. The $MV_{opt}$ may be associated with a specific current fractionalization $F_I^*$. The relationship among $I_{min}$, $F_I^*$, and $MV_{opt}$ may be represented as: $I_{min}=f(MV_{opt}, F_I^*)$. The minimal stimulation current $I_{min}$ and the current fractionalization $F_I^*$ that correspond the best metric value $MV_{opt}$ may be programmed into the neuromodulator to generate and deliver electrostimulation to the tissue.

Additional information regarding clinical effects may be found in U.S. patent application Ser. No. 15/902,163, filed Feb. 22, 2018, and entitled "Method and Apparatus For Clinical Effects-Based Targeting of Neurostimulation"; and U.S. Provisional Patent Application No. 62/598,558, filed Dec. 14, 2017, and entitled "Systems and Methods for Clinical Effect-Based Neurostimulation". U.S. patent application Ser. No. 15/902,163 and U.S. Provisional Patent Application No. 62/598,558 are hereby incorporated by reference in their entirety.

Figure 13:
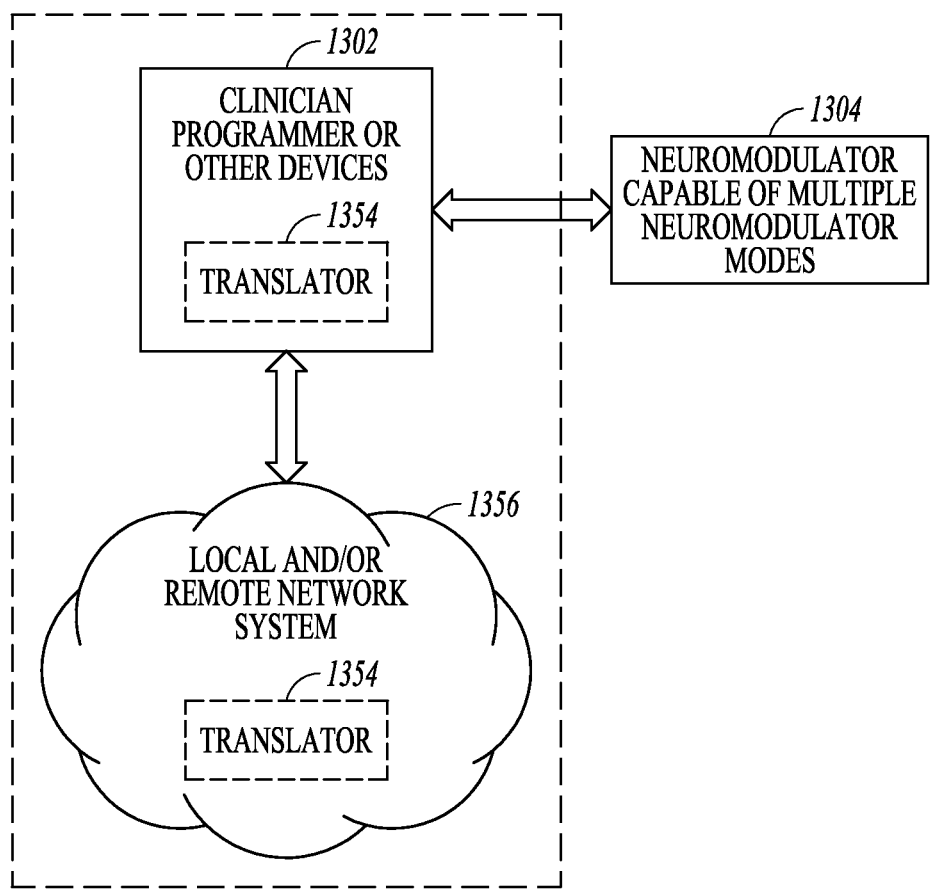
FIG. 13 illustrates an embodiment of a system for adjusting neuromodulation parameters used by a neuromodulator operably connected to a plurality of electrodes to modulate a neural target.

FIG. 13 illustrates an embodiment of a system for adjusting neuromodulation parameters used by a neuromodulator 1304 operably connected to a plurality of electrodes to modulate a neural target. The system has a translator 1354 for translating a first set of neuromodulation parameters specific for one type of neuromodulation polarity to a second set of neuromodulation parameters specific to another type of neuromodulation polarity. Thus, the translator 1354 accounts for the different reactions (e.g. thresholds, clinical effects, and the like) that different types of neural structures may have to different neuromodulation polarities. In some embodiments, the translator 1354 may reside in a clinician programmer 1302 or other device. In some embodiments, the translator 1354 may reside locally or remotely within a system networked with the clinician programmer 1302 or other device. Once the neuromodulation parameters have been translated, the system may keep the original set of neuromodulation parameters and the translated set of parameters (such as in different memory locations) to enable the system to deliver both types of neuromodulation, or the system may replace the original set of neuromodulation parameters with the translated set of neuromodulation parameters.

Figure 14:
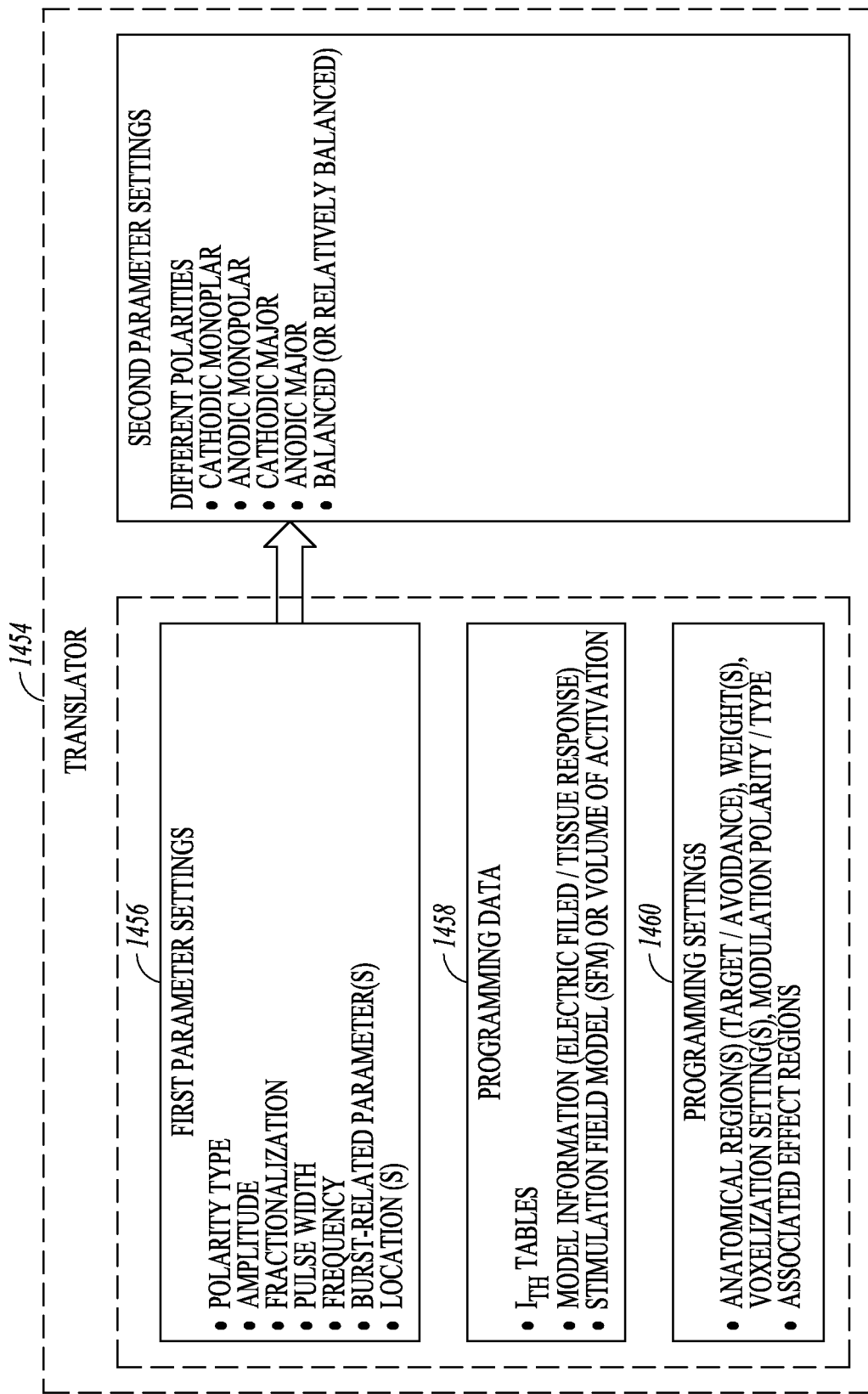
FIG. 14 illustrates functions of a translator such as may be implemented in the system of FIG. 13.

FIG. 14 illustrates functions of a translator such as may be implemented in the system of FIG. 13. Generally, the translator 1454 has access to at least some first parameter settings for a first polarity type, and is configured to generate second parameter settings for a different polarity type of neuromodulation. Examples of such polarity types include cathodic monopolar, anodic monopolar, cathodic major, anodic major, and balanced.

Some translator embodiments use only the pulse parameter data 1456 to generate the second parameter settings. Some translator embodiments access related data such as programming data 1458 (e.g. $I_{th}$ table, SFM, model information and the like) used to program the first pulse parameter data, and use that programming data to generate the second parameter settings. Some translator embodiments access related data such as programming settings that include anatomical regions 1460 (e.g. target, avoidance, weight, and the like) used to program the first pulse parameter data, and use those programming settings that include anatomical regions to generate the second parameter settings. These embodiments are described in more detail below.

Some translator embodiments translate the stimulation polarity of a program setting by inverting the polarity of any electrode that is in a cathodic or anodic state without changing the fractionalization or amplitude. Some translator embodiments may further multiply the amplitude of the first parameter settings by a scale factor to provide the amplitude of the second parameter settings, again without changing the fractionalization. The scale factor may depend on the polarity type of neuromodulation provided by the first parameter settings (e.g. whether the original fractionalization is mainly cathodic, mainly anodic or balanced). For example, the scale factor may be 1.5 if originally cathodic to accommodate higher energy needs of anodic energy to activate neural tissue, may be 0.66 if originally anodic to accommodate lower energy needs of cathodic energy activate neural tissue, or may be 1.0 if originally balanced. Some embodiments may further base the scale factor using one or more of: the polarity within the first parameter settings; the amplitude within the first parameter settings; a pulse width within the first parameter settings; a waveform within the first parameter settings; a frequency within the first parameter settings; at least one burst-related parameter within the first parameter settings; or one or more locations of modulation within the first parameter settings. An equation may be used having weighted values for these settings such that the scale factor is dependent on those settings. Some embodiments may determine the scale factor using a ratio between a first therapeutic range for the first parameter settings and a second therapeutic range for the second parameter settings. The first therapeutic range represents a range of amplitudes for the first parameter settings that extends from a therapeutic threshold to a side effect threshold. The second therapeutic range represents a range of amplitudes for the second parameter settings that extends from a therapeutic threshold to a side effect threshold. Some embodiment may determine a look-up table is used to determine the scale factor, and at least one of the polarity, the pulse width, the amplitude, the waveform, the frequency, the at least one burst-related parameter, or the one or more locations of modulation is used to index into the look-up table, the scale factor being a nearest value or an interpolated value.

For all cases, the scale factor may be determined and applied on an electrode by electrode basis. All the anode electrodes are turned to cathodes and their amplitude is multiplied by 0.67. All the cathode electrodes are turned into anodes and their amplitudes multiplied by 1.5

Rather than multiplying the amplitude by a scale factor, some embodiments use $I_{th}$ tables to determine the amplitude for the second parameter settings. For example, the amplitude for the second parameters may be determined by generating an $I_{th}$ table for the fractionalization in the first parameter settings and determining the maximum radius r of the SFM at the original amplitude. Then an $I_{th}$ table can be generated for the translated fractionalization (where the polarity of the electrical contribution for each active electrode is inverted), and finding the minimum $I_{th}$ value at the radius r, and using the amplitude as the amplitude for the second parameter settings.

Rather than multiplying the amplitude by a scale factor, some embodiments construct a first $I_{th}$ table characterizing spatial points for the fractionalization values in the first parameter settings, wherein the first parameter settings provide a first SFM, determine a volume of a SFM at the amplitude in the first parameter settings, construct a second $I_{th}$ table characterizing the spatial points for the second parameter settings to provide a second SFM, determine an amplitude that provides the second SFM with a volume that equals or approximately equals the first SFM, and use the determined amplitude in the second parameter settings.

Some translator embodiments invert the polarity of the original settings that may change the fractionalization of the current among the electrodes in the second parameter settings. For example, the system may have the ability to receive, via a user interface, at least one target region to be targeted using a neuromodulation field and zero or more avoidance regions to be avoided using the neuromodulation field, and determine fractionalization values for the second parameter settings to modulate the at least one target region and avoid the zero or more avoidance regions. The system may receive a polarity input indicating whether to provide anodic neuromodulation, cathodic neuromodulation or balanced or approximately balanced neuromodulation. The controller is configured to control a polarity of neuromodulation provided by the neuromodulator according to the received polarity input.

Some embodiments take the program settings for the first parameter settings, and return a new program inverts the polarity and that changes the fractionalization and amplitude, such that the fractionalization and amplitude in the second parameter settings are different than the fractionalization and amplitude in the first parameter settings. Some embodiments may determine a target from the SFM of the first parameter settings, and then find the matching fractionalization and amplitude for the different polarity type (e.g. inverted polarity). Some embodiments create an $I_{th}$ table for the original fractionalization, determine an initial fractionalization based on the original fractionalization but with the opposite polarity, determine the $I_{th}$ table for the initial fractionalization, determine the scaling factor that produces the minimum sum of the least squares difference between the original $I_{th}$ table and the $I_{th}$ table produced by the initial fractionalization, store the fractionalization, the scaling factor and the sum of the least squared differences, and optimize via an iterative process until stop criteria is achieved, the initial second fractionalization values into a second fractionalization values in the second table that has a least sum of the squared difference between the first table and the scaled second table. This step involves iteratively: (1) determining a different second fractionalization, (2) generating the Ith table for new second fractionalization, (3) calculating the scaling factor that produces the least squared differences, and (4) determine if stopping criteria have been met and either returning the best answer or going back to step 1. As the $I_{th}$ tables include a large number of $I_{th}$ values, various embodiments may only calculate the sum of the least squared differences for the part of the original Ith table with values below a limiting value. Some embodiments calculate the sum of the least squared differences for the part of the newly calculated $I_{th}$ table with values below a limiting value. Some embodiments calculate the sum of the least squared differences for the part of where both the original $I_{th}$ table and newly calculated $I_{th}$ table with values below a limiting value.

The limiting value may be entered by a user, or may be calculated by the system. The limiting value may be calculated from the amplitude in the first parameter settings. Example of rules include 1.5 times the original amplitude, the original amplitude squared if the original amplitude is greater than 1, or the square root of the original amplitude if the original amplitude is less than or equal to 1, or some other rule set. The limiting value may be calculated using the maximum value in the original Ith table, e.g. 0.5 times the maximum Ith value. The limiting value may be calculated using the maximum value of the original Ith table and the original amplitude, e.g. half way between the original amplitude and the maximum value. The limiting value may be calculated using the maximum value in the newly calculated Ith table, e.g. 0.5 times the maximum Ith value. The limiting value may be calculated using the maximum value of the newly calculated Ith table and the original amplitude, e.g. half way between the original amplitude and the maximum value. The limiting value may be calculated using the maximum value of the original Ith table, the maximum value of the newly calculated Ith table and the original amplitude, e.g. half way between the original amplitude and the minimum of the two maximum values.

Some embodiments may use a fractionalization look up table based on a virtual electrode that produces multi polar fractionalizations. A virtual electrode may be used to index into the fractionalization look-up table to produce multipolar fractionalizations. A virtual electrode is a method of converting steering coordinates into fractionalization. Each virtual electrode has a look up table for each lead type, so the lead type and virtual electrode type dictate which look up table to use. That look up table contains a sub-table for each electrode for that lead type. The axial and rotational coordinates are used as the index values into the sub-tables. The original table is an unbalance multi polar table. This table can be used as either Cathodic Major or Anodic Major by changing the sign of the fractionalization value on each electrode. Other tables could be created that matches the current monopolar steering states, where there would be a virtual electrode for each spread state. Through a user interface, a user may steer the virtual electrode according to the one or more virtual electrode steering parameters. The system may determine electrical current fractionalization across a plurality of electrodes based on the voltage field of the virtual electrode. Some embodiments use a fractionalization look up table that produces monopolar fractionalizations. Steering coordinates, including z axis, rotation, and spread coordinates, may be used to index into the fractionalization look-up table to produce monopolar fractionalizations.

Some translator embodiments use target and avoidance regions, known by the system and used to create the first parameter settings, to generate the second parameter settings. The system settings for the first parameter settings may include a target and 0 or more avoidance regions, where each region has an associated weight, which may be shared between regions, a background weight, possibly voxelization settings, and possibly a stimulation type.

The first parameter set may not include a known "stimulation type." Some embodiments use the known anatomical regions (e.g. target and avoidance), set a polarity type (e.g.

Anodic major) for neuromodulation, and then determine the fractionalization for the set polarity type to modulate the targeted region and avoid any avoidance regions.

Some system embodiments may identify the target and avoidance regions as being only applicable to particular polarity types. For example, one region may need to be avoided for cathodic major neuromodulation, but may not need to be avoided for anodic major neuromodulation. These target/avoidance regions may be considered polarity-specific regions that are specific to one or more of cathodic major neuromodulation, anodic major neuromodulation, or balanced or relatively balanced neuromodulation.

Target or avoidance regions that are applicable to a subset of the stimulation types may be associated with similar effect regions that are applicable to another, possibly overlapping, subset of the stimulation types. The associated regions are presented to the user as a single option (e.g. "Rigidity": associated regions that have the clinical effect on rigidity). Some embodiments of the system only use the target and avoidance regions that are applicable to polarity type of neuromodulation. Some embodiments may take an original set of programming settings, inverts the commanded stimulation type, and determines the fractionalization.

Various embodiment use fractionalization look-up tables that are specific to the neuromodulation. For example, some embodiments use a one-polarity major multipolar fractionalization look-up table to produce anodic major multipolar fractionalization or cathodic major multipolar fractionalization. Some embodiments a monopolar look-up table to produce anodic monopolar or cathodic monopolar fractionalizations. Some embodiments a monopolar look-up table to produce polarity-balanced fractionalizations. Producing balanced multipolar fractionalizations uses a lookup table created in a balanced manner. Similarly, there may be a monopolar table (same table can be used for anodic or cathodic monopolar) and a multipolar unbalanced (same table for anodic major or cathodic major). This table may have the preferred polarity at the target location, with the opposite polarity spread across the remaining electrodes in some manner. As with the other tables, the output would be either cathodic balanced or anodic balanced, by inverting the fractionalization values for each electrode.

Some of the previously-described translator embodiments may use language specific to DBS programming. However, the present subject matter is not limited to such DBS programming. By way of example, the following nonlimiting embodiments may be used to translate neuromodulation polarities for SCS therapies. For example, some SCS embodiments receive an input indicating whether to provide anodic neuromodulation, cathodic neuromodulation or balanced or approximately balanced neuromodulation, and determine electrode fractionalizations for the plurality of electrodes to provide at least one target pole for a neuromodulation field based on the neural target and the received input. The electrode fractionalizations for anodic neuromodulation may be based on an anodic stimulation field model representative of anodic activation threshold, the electrode fractionalizations for cathodic neuromodulation may be based on a cathodic stimulation field model representative of cathodic activation threshold, and the electrode fractionalizations for balanced or approximately balanced neuromodulation may be based on a balanced stimulation field model representative of balanced activation threshold. Some SCS embodiments may automatically translate the first parameter settings into the second parameter settings by changing the polarity for the at least one target pole, and changing the fractionalization and the amplitude. Some SCS embodiments may automatically translate the first parameter settings into the second parameter settings by determining a target pole for a first neuromodulation field that corresponds to the first parameter settings, and determining electrode fractionalizations and amplitude for the second parameter settings to provide the target pole for a second neuromodulation field. The target pole for the second neuromodulation field may have an inverted polarity from the at least one target pole for the first neuromodulation field. In some SCS embodiments, the parameters are automatically translated by constructing a first table for first fractionalization values in the first parameter settings to characterize spatial points, determining initial second fractionalization values for the second parameter settings based on the first fractionalization values wherein elements of the initial second fractionalization values have an opposite polarity with respect to elements of the first fractionalization values, constructing a second table using the initial second fractionalization values, determining a scaling factor for the initial fractionalization values in the second table that produces a minimum sum of the squares difference between the first table and the scaled second table, and optimizing the initial fractionalization values into a second fractionalization values in the second table that has a least sum of the squared difference between the first table and the scaled second table. Some SCS embodiments determine electrode fractionalizations using a fractionalization look-up table for a target multipole or using a fractionalization look-up table for a target monopole. Some embodiments automatically translate the first parameter settings into the second parameter settings by setting the neuromodulation polarity type to anodic major, and determining fractionalization values for the second parameter settings to modulate the neural target using anodic major neuromodulation.

Figure 15:
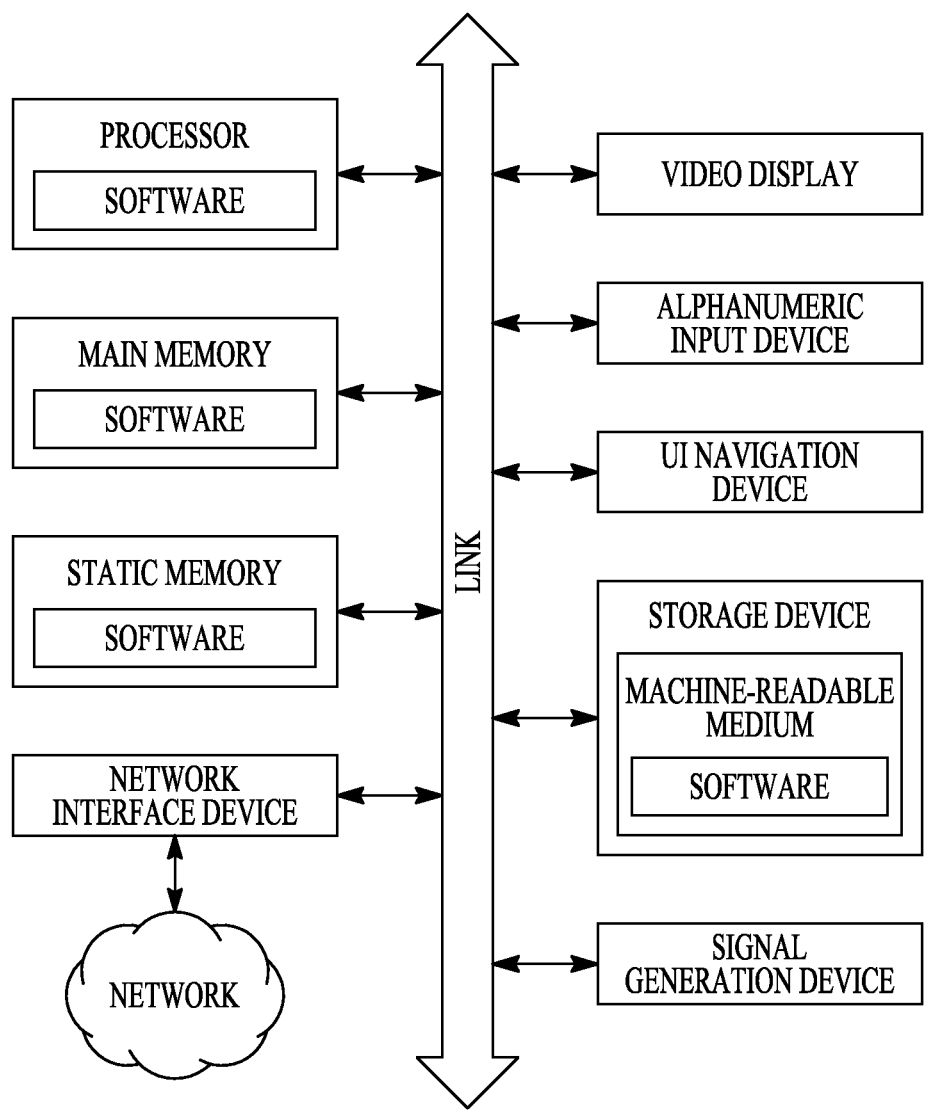
FIG. 15 is a block diagram illustrating a machine in the example form of a computer system, within which a set or sequence of instructions may be executed to cause the machine to perform any one of the methodologies discussed herein.

FIG. 15 is a block diagram illustrating a machine in the example form of a computer system, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by one or more processors (e.g., a computer) to individually or jointly execute instructions to perform any one or more of the methodologies discussed herein.

An example of a computer system includes at least one processor (e.g., a central processing unit (CPU), a graphics processing unit (GPU) or both, processor cores, compute nodes, etc.), a main memory and a static memory, which communicate with each other via a link (e.g., bus). The computer system may further include a video display unit, an alphanumeric input device (e.g., a keyboard), and a user interface (UI) navigation device (e.g., a mouse). In one embodiment, the video display unit, input device and UI navigation device are incorporated into a touch screen display. The computer system may additionally include a storage device (e.g., a drive unit), a signal generation device (e.g., a speaker), a network interface device, and one or more sensors (not shown), such as a global positioning system (GPS) sensor, compass, accelerometer, or other sensor. It will be understood that other forms of machines or apparatuses (such as IPG, RC, CP devices, and the like) that are capable of implementing the methodologies discussed in this disclosure may not incorporate or utilize every component depicted in FIG. 15 (such as a GPU, video display unit, keyboard, etc.).

The storage device includes a machine-readable medium on which is stored one or more sets of data structures and instructions (e.g., software) embodying or utilized by any one or more of the methodologies or functions described herein. The instructions may also reside, completely or at least partially, within the main memory, static memory, and/or within the processor during execution thereof by the computer system, with the main memory, static memory, and the processor also constituting machine-readable media.

While the machine-readable medium is illustrated in an example embodiment to be a single medium, the term "machine-readable medium" may include a single medium or multiple media (e.g., a centralized or distributed database, and/or associated caches and servers) that store the one or more instructions. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions may further be transmitted or received over a communications network using a transmission medium via the network interface device utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A method of delivering a neuromodulation therapy using a neuromodulator to modulate a neural target region without modulating an avoidance region, the method comprising:
    modulating the neural target region without modulating the avoidance region using a first neuromodulation field of a first polarity, the first neuromodulation field being generated by the neuromodulator and a first set of neuromodulation parameters, wherein the first set of neuromodulation parameters includes first fractionalization information, target region information and avoidance region information;
    receiving a translation trigger;
    automatically translating, in response to receiving the translation trigger and using both the target region information and the avoidance region information, the first set of neuromodulation parameters into a second set of neuromodulation parameters, wherein the second set of neuromodulation parameters includes second fractionalization information; and
    modulating the neural target region without modulating the avoidance region using a second neuromodulation field of a second polarity, the second neuromodulation field being generated by the neuromodulator and the second set of neuromodulation parameters,
    wherein the first fractionalization information and the second fractionalization information provide different fractionalizations defining different distributions of neuromodulation energy across a plurality of electrodes.

2. The method of claim 1, wherein neural tissue has a different tissue reaction to neuromodulation fields of different polarities, the method further comprising accounting for the different tissue reaction to determine a distribution of energy across the plurality of electrodes to provide the second neuromodulation field.

3. The method of claim 1, wherein the translating the first set of neuromodulation parameters into the second set of neuromodulation parameters includes determining an index using the first set of neuromodulation parameters, and using the index to determine fractionalizations for the second set of neuromodulation parameter settings.

4. The method of claim 3, wherein using the index includes indexing into a fractionalization look-up table to determine fractionalizations for the second set of neuromodulation parameter settings.

5. The method of claim 3, wherein the index is determined using a virtual electrode based on the first set of neuromodulation parameter settings.

6. The method of claim 3, wherein the index is determined using steering coordinates based on the first set of neuromodulation parameter settings.

7. The method of claim 1, wherein the first and second sets of neuromodulation parameter settings respectively include different first and second combinations of active electrodes for use to pass neuromodulation energy to the neural target.

8. The method of claim 1, wherein the automatically translating the first set of neuromodulation parameters into a second set of neuromodulation parameters includes changing polarity for each active electrode.

9. The method of claim 1, wherein the automatically translating the first set of neuromodulation parameters into a second set of neuromodulation parameters includes changing the polarity of the neuromodulation, changing the fractionalization and changing the amplitude.

10. The method of claim 1, wherein the automatically translating the first set of neuromodulation parameters into a second set of neuromodulation parameters includes multiplying the amplitude by a scale factor, wherein the scale factor is determined based on whether the first parameter settings are characterized as cathodic, characterized as anodic, or characterized as balanced or relatively balanced between cathodic and anodic.

11. The method of claim 1, wherein the neuromodulation therapy includes a Deep Brain Stimulation (DBS) therapy.

12. A non-transitory computer-readable medium having computer executable instructions stored thereon that, when executed by at least one processor, cause the at least one processor to perform a method for delivering a neuromodulation therapy to modulate a neural target region without modulating an avoidance region, wherein the method includes:
- modulating the neural target without modulating the avoidance region using a first neuromodulation field of a first polarity, the first neuromodulation field being generated by the neuromodulator and a first set of neuromodulation parameters, wherein the first set of neuromodulation parameters includes first fractionalization information, target region information and avoidance region information;
- receiving a translation trigger;
- automatically translating, in response to receiving the translation trigger and using both the target region information and the avoidance region information, the first set of neuromodulation parameters into a second set of neuromodulation parameters; and
- modulating the neural target using a second neuromodulation field of a second polarity, the second neuromodulation field being generated by the neuromodulator and the second set of neuromodulation parameters,
- wherein the first fractionalization information and the second fractionalization information provide different fractionalizations defining different distributions of neuromodulation energy across a plurality of electrodes.

13. The non-transitory computer-readable medium of claim 12, wherein neural tissue has a different tissue reaction to neuromodulation fields of different polarities, the method further comprising accounting for the different tissue reaction to determine a distribution of energy across the plurality of electrodes to provide the second neuromodulation field.

14. The non-transitory computer-readable medium of claim 12, wherein the translating the first set of neuromodulation parameters into the second set of neuromodulation parameters includes determining an index using the first set of neuromodulation parameters, and using the index to determine fractionalizations for the second set of neuromodulation parameter settings.

15. The non-transitory computer-readable medium of claim 14, wherein using the index includes indexing into a fractionalization look-up table to determine fractionalizations for the second set of neuromodulation parameter settings.

16. The non-transitory computer-readable medium of claim 14, wherein the index is determined using a virtual electrode based on the first set of neuromodulation parameter settings, or is determined using steering coordinates based on the first set of neuromodulation parameter settings.

17. The non-transitory computer-readable medium of claim 12, wherein the first and second sets of neuromodulation parameter settings respectively include different first and second combinations of active electrodes for use to pass neuromodulation energy to the neural target.

18. The non-transitory computer-readable medium of claim 12, wherein the neuromodulation therapy includes a Deep Brain Stimulation (DBS) therapy.

19. A system for delivering a neuromodulation therapy to modulate a neural target region without modulating an avoidance region, the system comprising a neuromodulation device configured to use a first set of neuromodulation parameters to modulate the neural target without modulating the avoidance region using a first neuromodulation field of a first polarity, wherein the first set of neuromodulation parameters includes first fractionalization information, target region information and avoidance region information, wherein the system is configured to automatically translate, in response to receiving a translation trigger and using both the target region information and the avoidance region information, the first set of neuromodulation parameters into a second set of neuromodulation parameters, wherein the second set of neuromodulation parameters includes second fractionalization information, and the neuromodulation device is configured to modulate the neural target region without modulating the avoidance region using a second neuromodulation field of a second polarity, the second neuromodulation field being generated by the neuromodulator and the second set of neuromodulation parameters, wherein the first fractionalization information and the second fractionalization information provide different fractionalizations defining different distributions of neuromodulation energy across a plurality of electrodes.

20. The system of claim 19, wherein the neuromodulation therapy includes a Deep Brain Stimulation (DBS) therapy.

* * * * *